(12) United States Patent
Guenther et al.

(10) Patent No.: US 9,877,956 B2
(45) Date of Patent: Jan. 30, 2018

(54) ANTIVIRAL COMPOUNDS AND METHODS OF USE THEREOF

(71) Applicant: Trana Discovery, Inc., Cary, NC (US)

(72) Inventors: Richard H. Guenther, Cary, NC (US); Daniel Sternbach, Chapel Hill, NC (US); Steven E. Peterson, Cary, NC (US)

(73) Assignee: TRANA DISCOVERY, INC., Cary, NC (US)

( * ) Notice: Subject to any disclaimer, the term of this patent is extended or adjusted under 35 U.S.C. 154(b) by 0 days.

(21) Appl. No.: 14/761,503

(22) PCT Filed: Jan. 17, 2014

(86) PCT No.: PCT/US2014/012055
§ 371 (c)(1),
(2) Date: Jul. 16, 2015

(87) PCT Pub. No.: WO2014/113675
PCT Pub. Date: Jul. 24, 2014

(65) Prior Publication Data
US 2015/0359786 A1    Dec. 17, 2015

(51) Int. Cl.
A61K 31/47 (2006.01)
A61K 45/06 (2006.01)
A61K 31/366 (2006.01)

(52) U.S. Cl.
CPC ............ *A61K 31/47* (2013.01); *A61K 31/366* (2013.01); *A61K 45/06* (2013.01)

(58) Field of Classification Search
CPC ....... A61K 31/47; A61K 45/06; A61K 31/366
See application file for complete search history.

(56) References Cited

U.S. PATENT DOCUMENTS

2003/0149069 A1    7/2003  Li et al.
2007/0054355 A1*   3/2007  Reiss .................. C07K 14/705
                                                  435/69.1

OTHER PUBLICATIONS

Coffin JM, Hughes SH, Varmus HE, editors. Retroviruses. Cold Spring Harbor (NY): Cold Spring Harbor Laboratory Press; 1997.*
Panchal, Rekha G. et al.; "Development of high-content imaging assays for lethal viral pathogens"; Journal of Biomolecular Screening, 2010, 15(7), pp. 755-765.
AC1LFMGY, 1-(3,4-dihydroquinolin-2-yl)-2-phenylhydrazine, Jul. 9, 2005 [on-line]; 1-27; http://pubchem.ncbi.nlm.nih.gov/summary/summary.cgi?cid=780386>.
5-[ ( 5-iodo-2-furyl)methylene]-2,2-dimethyl-1 ,3-dioxane-4,6-dione, Jul. 8, 2005 [on-line]; http://pubchem.ncbi.nlm.nih.gov/summary/summary.cgi?cid=687628>.

* cited by examiner

Primary Examiner — Savitha Rao
Assistant Examiner — Angela Brown-Pettigrew
(74) Attorney, Agent, or Firm — David Bradin; Andrews Kurth Kenyon LLP

(57) ABSTRACT

Inhibitors of retroviral propagation, methods of treatment and prevention of retroviral infections using the inhibitors, and pharmaceutical compositions including the inhibitors, are disclosed.

9 Claims, 10 Drawing Sheets

ANTIVIRAL COMPOUNDS AND METHODS OF USE THEREOF

CROSS-REFERENCE TO RELATED APPLICATIONS

This application is a U.S. national phase entry, under the provisions of 35 U.S.C. § 371, of International Patent Application No. PCT/US2014/012055 filed Jan. 17, 2014, which in turn claims priority to U.S. Patent Application No. 61/753,794 filed Jan. 17, 2013. The disclosures of such international patent application and United States priority patent application are hereby incorporated herein by reference in their respective entireties, for all purposes.

FIELD

The invention generally relates to antiviral compounds, compositions including the compounds, and methods of treatment using the compounds.

BACKGROUND

The primate lentiviruses include the human immunodeficiency viruses types 1 and 2 (HIV-1 and HIV-2) and simian immunodeficiency viruses (SIVs) (Barre-Sinoussi, F., et al. (1983) Science 220:868-871; Clavel, F. (1987) AIDS 1:135-140; Daniel, M. D., et al. (1985) Science 228:1201-1204; Desrosiers, R. C. (1990) Ann. Rev. Immunol. 8: 557-578; Gallo, R. C, et al. (1984) Science 224:500-503). HIV-1 and HIV-2 infect humans, HIV-1-like viruses infect chimpanzees, and SIV variants infect African monkeys. Humans infected by HIV-1 and HIV-2 and Asian macaques infected by certain SIV strains often develop life-threatening immunodeficiency due to depletion of CD4-positive T lymphocytes (Fauci, A., et al. (1984) Ann. Int. Med. 100:91-106; Letvin, N. L., et al. (1985) Science 230:71-739, 19).

In humans, HIV infection causes Acquired Immunodeficiency Syndrome (AIDS), an incurable disease in which the body's immune system breaks down leaving the victim vulnerable to opportunistic infections, e.g., pneumonia and certain cancers, e.g., Kaposi's Sarcoma. AIDS is a major global health problem. The Joint United Nations Programme on HIV/AIDS (HIV/AIDS) estimates that there are now over 34 million people living with HIV or AIDS worldwide; some 28.1 million of those infected individuals reside in impoverished subSaharan Africa. In the United States, approximately one out of every 500 people are infected with HIV or have AIDS. Since the beginning of the epidemic, AIDS has killed nearly 19 million people worldwide, including some 425,000 Americans. AIDS has replaced malaria and tuberculosis as the world's deadliest infectious disease among adults and is the fourth leading cause of death worldwide.

There remains a need for the identification of inhibitors of retroviral infection.

SUMMARY

Compounds which are inhibitors of retroviral propagation are disclosed. Methods of treating and/or preventing retroviral infection using the inhibitors of retroviral propagation, and pharmaceutical compositions including the inhibitors and a pharmaceutically-acceptable carrier, are also disclosed. Combination therapy using one or more of the inhibitors, and a second anti-retroviral compound, are also disclosed.

The compounds inhibit retroviral propagation by inhibiting retroviral reverse transcription, viral recruitment of the retroviral primer used in translation, human tRNA$^{Lys3}$, inhibiting the final packaging and assembly of new virions, and/or inhibiting the binding of a host cell tRNA to a target nucleic acid molecule.

The inhibitory activity of the compounds can be evaluated using methods for screening inhibitors of retroviral propagation. Such methods may involve forming a mixture comprising a linear sequence of a tRNA anticodon stem loop fragment, a nucleic acid molecule capable of binding to the tRNA anticodon stem loop fragment, and a test compound. The mixture is incubated under conditions that allow binding of the tRNA anticodon stem loop fragment and the nucleic acid molecule in the absence of the test compound. One can then determine whether or not a test compound inhibits the propagation of a retrovirus. Inhibition of binding of the tRNA ASL fragment and the target nucleic acid molecule is indicative of the test compound being an inhibitor of retroviral propagation.

DETAILED DESCRIPTION

Figure 1:
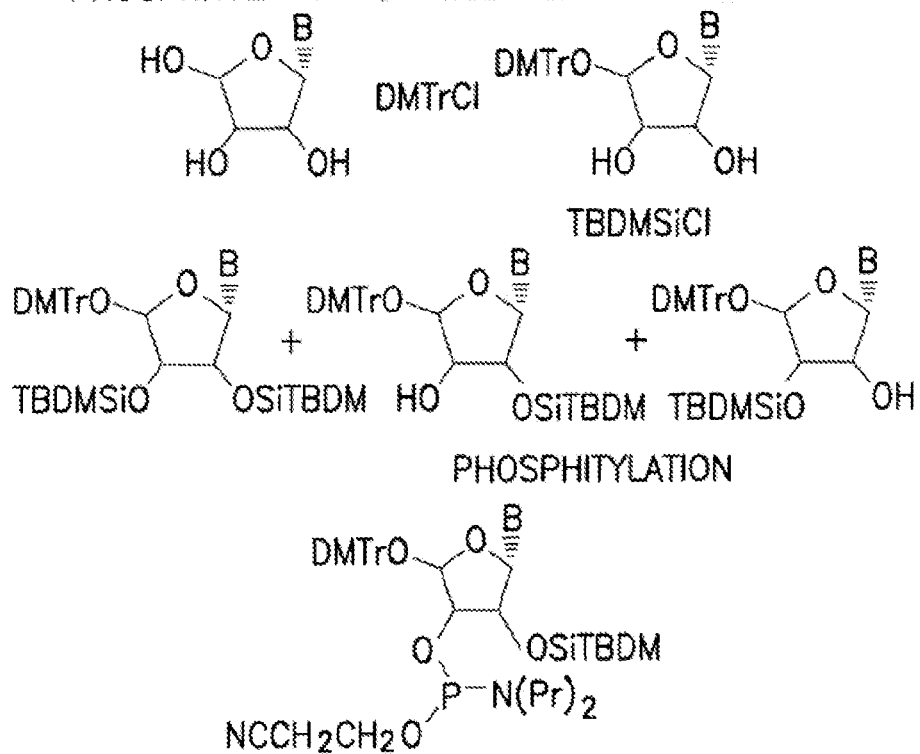
FIG. 1 provides a schematic representation of the protection of the modified nucleotides prior to synthesis of the RNA oligomer. Panel A illustrates protection with trifluoryl acetic acid. Panel B illustrates protection with benzoyl. Panel C illustrates the general protection of the ribose hydroxyl groups.
Figure 2:
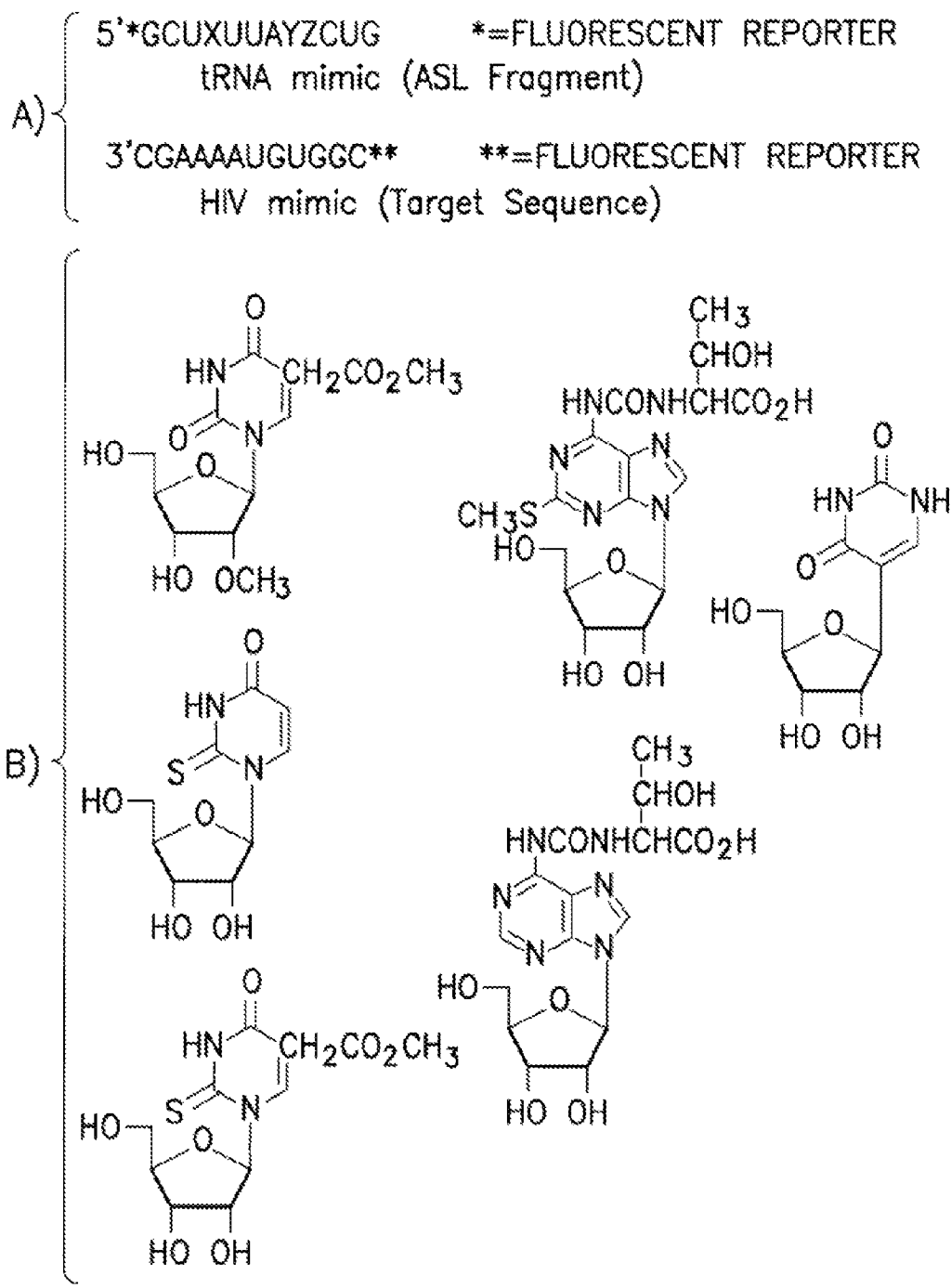
FIG. 2A provides a representation of a labeled tRNA fragment and a corresponding target sequence.
FIG. 2B provides structures of several representative modified nucleosides.

The present invention relates to compounds which inhibit retroviral propagation, compositions including the compounds, and methods of treating and/or preventing retroviral infection using the compounds. Viral propagation can be inhibited by inhibiting reverse transcription, viral replication, translation of viral RNA into proteins, recruitment of human tRNA$^{Lys3}$, packaging and assembly of new virions, and/or inhibiting the binding of a host cell tRNA to a target nucleic acid molecule.

Prior to describing this invention in further detail, however, the following terms will first be defined.

Definitions

As used herein, an "inhibitor" refers to any compound capable of preventing, reducing, or restricting retroviral propagation. An inhibitor may inhibit retroviral propagation, for example, by preventing, reducing or restricting retroviral reverse transcription. In some embodiments, the inhibition is at least 20% (e.g., at least 50%, 70%, 80%, 90%, 95%, 98%, 99%, 99.5%) of the retroviral propagation as compared to the propagation in the absence of the inhibitor. In one aspect, an inhibitor prevents, reduces, or restricts the binding of a tRNA, or fragment thereof, to a target nucleic acid molecule. Inhibitors can also affect recruitment of human tRNA$^{Lys3}$, translation of viral RNA into proteins, and/or final packaging and assembly of virions. Assays for analyzing inhibition are described herein and are known in the art.

An "RNA-dependent DNA polymerase" or "reverse transcriptase" is an enzyme that can synthesize a complementary DNA copy ("cDNA") from an RNA template. All known reverse transcriptases also have the ability to make a complementary DNA copy from a DNA template (target nucleic acid); thus, they are both RNA- and DNA-dependent DNA polymerases.

As used herein, a "label" or "detectable label" is any composition that is detectable, either directly or indirectly, for example, by spectroscopic, photochemical, biochemical, immunochemical, or chemical means. Useful labels include, but are not limited to, radioactive isotopes (for example, 32p, 35S, and 3H), dyes, fluorescent dyes (for example, Cy5 and Cy3), fluorophores (for example, fluorescein), electron-dense reagents, enzymes and their substrates (for example, as commonly used in enzyme-linked immunoassays, such as, alkaline phosphatase and horse radish peroxidase), biotin-streptavidin, digoxigenin, or hapten; and proteins for which antisera or monoclonal antibodies are available. Moreover, a label or detectable moiety can include an "affinity tag" that, when coupled with the target nucleic acid and incubated with a test compound or compound library, allows for the affinity capture of the target nucleic acid along with molecules bound to the target nucleic acid. One skilled in the art will appreciate that an affinity tag bound to the target nucleic acid has, by definition, a complimentary ligand coupled to a solid support that allows for its capture. For example, useful affinity tags and complimentary partners include, but are not limited to, biotin-streptavidin, complimentary nucleic acid fragments (for example, oligo dT-oligo dA, oligo T-oligo A, oligo dG-oligo dC, oligo G-oligo C), aptamers, or haptens and proteins for which antisera or monoclonal antibodies are available. The label or detectable moiety is typically bound, either covalently, through a linker or chemical bound, or through ionic, van der Waals or hydrogen bonds to the molecule to be detected.

The terms "alkyl", "aryl" and other groups refer generally to both unsubstituted and substituted groups unless specified to the contrary.

Unless specified otherwise, alkyl groups are hydrocarbon groups and are preferably $C_1$-$C_{15}$ (that is, having 1 to 15 carbon atoms) alkyl groups, which can be branched or unbranched, acyclic or cyclic. The above definition of an alkyl group and other definitions would apply also when the group is a substituent on another group (for example, an alkyl group as a substituent of an alkylamino group or a dialkylamino group).

The term "aryl" refers to any functional group or substituent derived from a simple aromatic ring, such as phenyl, thiophenyl, indoyl, etc.

The term "alkenyl" refers to a straight or branched chain hydrocarbon group with at least one double bond, preferably with 2-15 carbon atoms.

The term "alkynyl" refers to a straight or branched chain hydrocarbon group with at least one triple bond, preferably with 2-15 carbon atoms.

The terms "alkylene," "alkenylene" and "alkynyllene" refer to bivalent forms of alkyl, alkenyl, and alkynyl groups, respectively.

The terms "halogen" or "halo" refer to fluoro, chloro, bromo, or iodo.

Substituent groups building off of the hydrocarbon groups include alkoxy, aryloxy, acyloxy, haloalkyl, perfluoroalkyl, fluorine, chlorine, bromine, carbamoyloxy, hydroxyl, nitro, cyano, cyanoalkyl, azido, azidoalkyl, formyl, hydrazine, hydroxyalkyl, alkoxyalkyl, and the like.

I. Antiviral Compounds

The compounds generally have one of the following formulas:

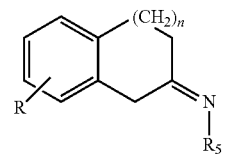

Formula I

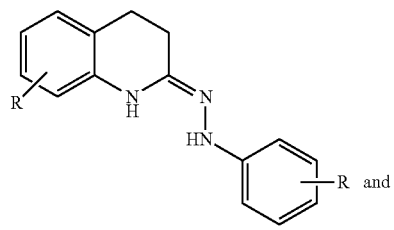

Formula IA

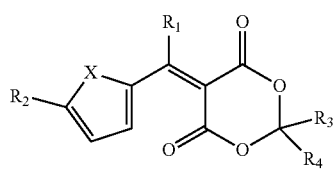

Formula II wherein:

R is selected from the group consisting of hydrogen, lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, heterocyclic, alkylaryl, arylalkyl, hydroxyl, nitro, cyano, cyanoalkyl, azido, azidoalkyl, formyl, hydrazino, halo (F, Cl, Br, or I), OR', N(R')$_2$, SR', COOR', COR', OCOR', NHCOR', N(COR')COR', SCOR', OCOOR', and NHCOOR', wherein each R' is independently H, a lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, alkylaryl, or arylalkyl, wherein the groups can be substituted with one or more substituents as defined above), $R_1$ is selected from the group consisting of hydrogen, lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, heterocyclic, alkylaryl, arylalkyl, $R_2$ is selected from the group consisting of hydrogen, lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, heterocyclic, alkylaryl, arylalkyl, hydroxyl, nitro, cyano, cyanoalkyl, azido, azidoalkyl, formyl, hydrazino, halo (F, Cl, Br, or I), OR', N(R')$_2$, SR', COOR', COR', OCOR', NHCOR', N(COR')COR', SCOR', OCOOR', and NHCOOR', wherein each R' is independently H, a lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, alkylaryl, or arylalkyl $R_3$ and $R_4$, are, independently, the same or different, and are selected from hydrogen and $C_{1-6}$ alkyl, $R_5$ is —$OR_6$, —$NHR_6$, —$CH_2R_6$, or —$CH_2CH_2R_6$, $R_6$=—$CH_2CO_2H$, —$CH_2NR_3R_4$, phenyl ("Ph"), or PhR, wherein the R moiety is ortho, meta, or para to the —O, —NH, —$CH_2$, or —$CH_2CH_2$ moiety attached to the phenyl substituent in $R_5$, such as

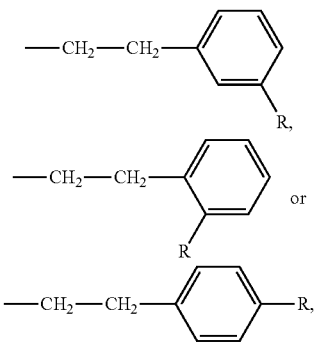

and similar compounds where the —$CH_2$—$CH_2$— is replaced with O, N, or —$CH_2$—, n is 0, 1, or 2, and X is NR', O, S, Se, or $CR_2$, and pharmaceutically acceptable salts thereof.

In one embodiment of the compounds of Formula I, the compound has the following structure:

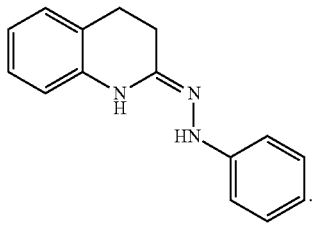 [SMILES: c1ccc(N/N=C2/CCc3ccccc3N2)cc1]

In one embodiment of the compounds of Formula II, X is O.

In one embodiment of the compounds of Formula II, the compound has the following structure:

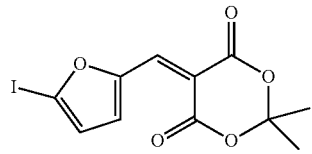 [SMILES: CC1(C)OC(=O)C(=Cc2ccc(I)o2)C(=O)O1]

In one embodiment, these substituents are, independently, the same or different, and are selected from hydrogen, alkyl, cycloalkyl, aryl, arylalkyl, alkylaryl, heterocyclic, heteroaryl, alkenyl, alkynyl, halo (F, Cl, Br, I), OR', N(R')$_2$, SR', OCOR', NHCOR', N(COR')COR', SCOR', OCOOR', and NHCOOR', wherein each R' is independently H, a lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, alkylaryl, or arylalkyl, wherein the groups can be substituted with one or more substituents as defined above).

In some embodiments, the compounds may have one or more chiral centers. In such embodiments, compounds that are enantiomerically enriched, or which are racemic mixtures, are contemplated. Such enantiomerically enriched compounds and racemic mixtures are within the scope of the invention. Separation of individual stereoisomers from racemic mixtures can be performed using known purification methods, including enzymatic resolution, chiral chromatography, formation and later separation of diastereomeric salts (for example, by reacting an amine with brucine), and the like.

II. Synthetic Methods

Preparing the Compounds of Formula I

A representative synthetic strategy for preparing the compounds of Formula I is shown below.

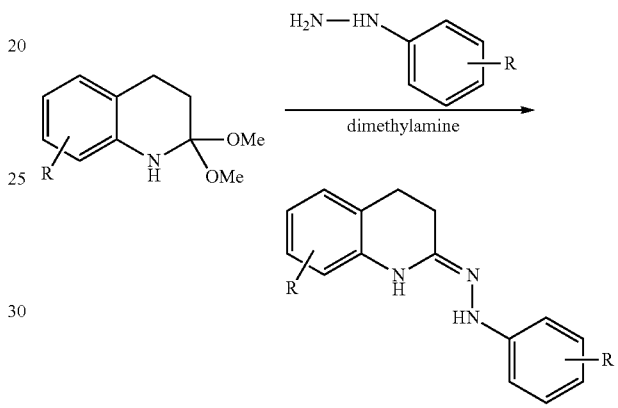

The condensation of the aryl-$NH_2$—$NH_2$ moiety with the dimethyl acetal of the amide can yield a mixture of the desired amidine and an undesired imidate ester depending on the temperature, solvent, and structure of the aryl-$NH_2$—$NH_2$ moiety. It is possible to suppress the formation of imidate ester by performing the reaction in the presence of excess dimethyl amine. The reaction is a variation of the chemistry described in J. R. Harjani, C. Liang, P. G. Jessop, J. Org. Chem., 2011, 76, 1683-1691.

Functional groups present on the dimethyl acetal starting material that might otherwise react with the aryl-$NH_2$—$NH_2$ moiety can be protected during the amidine synthesis, and deprotected afterwards.

Suitable protecting groups include those described in Greene and Wuts, Protective Groups in Organic Synthesis, 3rd Edition, June 1999, John Wiley & Sons Inc., the contents of which are hereby incorporated by reference.

Preparing the Compounds of Formula II

A representative synthetic strategy for preparing the compounds of Formula II is shown below.

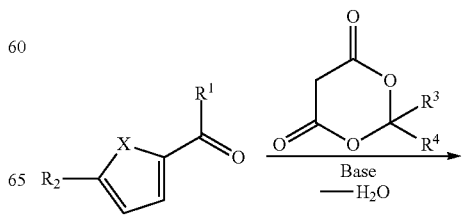

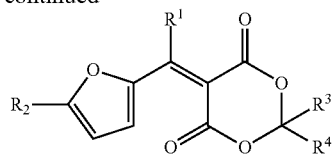

The methylene group between the two carbonyls includes a relatively acidic carbon atom, so this carbon atom is readily deprotonated to form an enolate, which can react with the —C(O)R$_1$ moiety. This forms a hydroxy group, which, upon loss of water, forms the conjugated double bond.

Functional groups that might react with enolate ions can be protected before the coupling step, and deprotected after the coupling step. Suitable protecting groups include those described in Greene and Wuts, Protective Groups in Organic Synthesis, 3rd Edition, June 1999, John Wiley & Sons Inc., the contents of which are hereby incorporated by reference.

Aromatic Substitution Reactions—Functionalization of Aryl Rings

Where it is desirable to provide substitution on the aryl rings, electrophilic aromatic substitution can be used to provide certain desired functionality. For example, alkyl, aryl, heteroaryl, alkaryl, arylalkyl, alkenyl, alkynyl, and acyl groups can be added using Friedel-Crafts alkylation/arylation/acylation reactions. Other electrophilic aromatic substitution reactions can be used, for example, to provide halogens, such as by forming chloronium or bromonium ions in situ and reacting them with the aromatic ring, or by forming sulfonium or nitronium ions to provide sulfonyl or nitro groups.

Friedel Crafts alkylation is conducted using an appropriate halo-alkyl moiety, and a Lewis acid. The alkyl moiety forms a carbocation, and electrons from the aryl ring form a bond with the carbocation, placing a positive charge on the aryl ring. The aryl ring then loses a proton. Alkyl and alkaryl moieties (such as benzyl moieties) can be added in this fashion.

Friedel Crafts acylation is similar, but uses an acid halide, such as an acid chloride, to place a ketone moiety on the ring. The acid halide can be an alkyl acid, such as acetic acid, propionic acid, butyric acid, and the like, or can be an aromatic acid, such as benzoic acid, p-toluic acid, and the like.

Friedel Crafts arylation (also known as the Scholl reaction) is a coupling reaction with two aryl rings, catalyzed by a Lewis acid. The proton lost during the coupling reaction serves as an additional catalyst. Typical Reagents are iron (III) chloride in dichloromethane, copper(II) chloride, PIFA and boron trifluoride etherate in dichloromethane, Molybdenum(V) chloride and lead tetraacetate with BF$_3$ in acetonitrile.

Electrophilic Aromatic Substitution on 5-Membered Heteroaryl Rings

Unsubstituted pyrrole, furan, and thiophene are usually obtained from petroleum. They may be converted into substituted aromatic heterocycles through an electrophilic substitution. In this respect, furan, thiophene, pyrrole and their derivatives are all highly activated compared to benzene. These compounds all contain an atom with an unshared pair of electrons (oxygen, sulphur, or nitrogen) as a member of the aromatic ring, which substantially increases the stability of the cationic intermediate. As with benzene rings, these substitutions take place by an initial electrophile addition, followed by a proton loss from the "onium" intermediate to regenerate the aromatic ring. The aromatic five-membered heterocycles all undergo electrophilic substitution, with a general reactivity order: pyrrole>>furan>thiophene>benzene. Substitution is typically at the 2-position.

Examples of electrophilic substitutions to pyrrole are the Pictet-Spengler reaction and the Bischler-Napieralski reaction.

Additionally, substituted aromatic five-membered-ring heterocycles may also be synthesized through the cyclization of 1,4-diketones in combination with ammonia, amines, phosphorus pentoxide, or phosphorus pentasulfide. The ring-closure is preceded by dehydration (condensation), which then yields the two double bonds and, thus, the aromatic π system. The formation of the energetically favored aromatic system is one of the driving forces of the reaction.

Enantiomeric Purification

As used herein, the term "enantiomerically pure" refers to a nucleotide composition that comprises at least approximately 95%, and, preferably, approximately 97%, 98%, 99% or 100% of a single enantiomer of that nucleotide.

As used herein, the term "substantially free of" or "substantially in the absence of" refers to a nucleotide composition that includes at least 85 to 90% by weight, preferably 95% to 98% by weight, and, even more preferably, 99% to 100% by weight, of the designated enantiomer of that nucleotide. In a preferred embodiment, the compounds described herein are substantially free of enantiomers.

Similarly, the term "isolated" refers to a nucleotide composition that includes at least 85 to 90% by weight, preferably 95% to 98% by weight, and, even more preferably, 99% to 100% by weight, of the nucleotide, the remainder comprising other chemical species or enantiomers.

The compounds described herein may have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective nucleoside, then derivatize the nucleoside to form the compounds described herein, or purify the nucleotides themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.
  i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

III. Methods of Treatment

The compounds described herein are capable of inhibiting viral propagation. The retroviral propagation can be inhibited by inhibiting retroviral reverse transcription, viral recruitment of the retroviral primer used in translation, human tRNA$^{Lys3}$, inhibiting the final packaging and assembly of new virions, and/or inhibiting the binding of a host cell tRNA to a target nucleic acid molecule.

Accordingly, these compounds can be used in methods to treat patients suffering from retroviral infections. That is, a retroviral viral infection can be treated or prevented by administering one or more inhibitors of retroviral propagation, for example, inhibitors of retroviral reverse transcription, binding to host cell tRNA and a target nucleic acid molecule, recruitment of the retroviral primer, human tRNA$^{Lys3}$, viral RNA translation into viral proteins, and final viral packaging and assembly of virions. Treatment of viral disease has not been heretofore accomplished by using such inhibitors.

The compounds can be used to treat or prevent viral infections, including infections by retroviruses, and/or to inhibit viral replication, propagation, reverse transcription, mRNA translation, and/or final viral packaging and assembly. Retroviruses for which inhibitors can be identified by the methods disclosed herein include any viruses having RNA as their primary genetic material and use reverse transcription to produce DNA. Such viruses include, but are not limited to, Feline Immunodeficiency Virus (FIV), Simian Immunodeficiency Virus (SIV), Avian Leucosis Virus, Feline Leukemia Virus, Walleye Dermal Sarcoma Virus, Human T-Lymphotropic Virus, and Human Immunodeficiency Viruses (HIV). In a preferred aspect, the retrovirus is HIV. HIV can be any strain, form, subtype or variation in the HIV family. HIV viruses include, but are not limited to, HIV-I, HIV-II, HIV-III (also known as HTLV-II, LAV-I, LAV-2), and the like.

The compounds can also be used as adjunct therapy in combination with existing therapies in the management of the aforementioned types of viral infections. In such situations, it is preferably to administer the active ingredients to a patient in a manner that optimizes effects upon viruses, including mutated, multi-drug resistant viruses, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

Retroviruses whose infection can be treated or prevented using the inhibitors described herein include any viruses having RNA as their primary genetic material and use reverse transcription to produce DNA. Such viruses include, but are not limited to, Feline Immunodeficiency Virus (FIV), Simian Immunodeficiency Virus (SIV), Avian Leucosis Virus, Feline Leukemia Virus, Walleye Dermal Sarcoma Virus, Human T-Lymphotropic Virus, and Human Immunodeficiency Viruses (HIV). In a preferred aspect, the retrovirus is HIV. HIV can be any strain, form, subtype or variation in the HIV family. HIV viruses include, but are not limited to, HIV-I, HIV-II, HIV-III (also known as HTLV-II, LAV-I, LAV-2), mutated versions thereof, and the like.

Inhibitors of HIV are also active against the hepatitis B virus (HBV), and can be used in methods of treating and/or preventing HBV infection, and pharmaceutical compositions intended for this use.

IV. Pharmaceutical Compositions

The inhibitory compounds as described herein can be incorporated into pharmaceutical compositions and used to treat or prevent a viral infection, such as a retroviral infection. The pharmaceutical compositions described herein include the inhibitory compounds as described herein, and a pharmaceutically acceptable carrier and/or excipient.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intravenously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where viral infections are located. The compounds described herein are very potent at treating these viral infections.

In certain circumstances, the compounds described herein can be employed as part of a pharmaceutical composition with other compounds intended to prevent or treat a particular viral infection, i.e., combination therapy. In addition to effective amounts of the compounds described herein, the pharmaceutical compositions can also include various other components as additives or adjuncts.

Combination or Alternation Therapy

In one embodiment, the compounds of the invention can be employed together with at least one other antiviral agent, chosen from entry inhibitors, reverse transcriptase inhibitors, protease inhibitors, and immune-based therapeutic agents.

For example, when used to treat or prevent HIV infection, the active compound or its prodrug or pharmaceutically acceptable salt can be administered in combination or alternation with another anti-HIV agent. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Combination therapy may be administered as (a) a single pharmaceutical composition which comprises an inhibitory compound as described herein, at least one additional pharmaceutical agent described herein, and a pharmaceutically acceptable excipient, diluent, or carrier; or (b) two separate pharmaceutical compositions comprising (i) a first composition comprising an inhibitory compound as described herein and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing viral disease, the inhibitory compound(s) can be administered together with at least one other antiviral agent as part of a unitary pharmaceutical composition. Alternatively, it can be administered apart from the other antiviral agents. In this embodiment, the inhibitory compound and the at least one other antiviral agent are administered substantially simultaneously, i.e. the compounds are administered at the same time or one after the other, so long as the compounds reach therapeutic levels for a period of time in the blood.

Combination therapy involves administering the inhibitory compound, as described herein, or a pharmaceutically acceptable salt or prodrug of the inhibitory compound, in combination with at least one anti-viral agent, ideally one which functions by a different mechanism than the inhibitors of viral propagation described herein.

Representative Antiviral Agents

Some antiviral agents which can be used for combination therapy include agents that interfere with the ability of a virus to infiltrate a target cell. The virus must go through a sequence of steps to do this, beginning with binding to a specific "receptor" molecule on the surface of the host cell and ending with the virus "uncoating" inside the cell and releasing its contents. Viruses that have a lipid envelope must also fuse their envelope with the target cell, or with a vesicle that transports them into the cell, before they can uncoat.

There are two types of active agents which inhibit this stage of viral replication. One type includes agents which mimic the virus-associated protein (VAP) and bind to the cellular receptors, including VAP anti-idiotypic antibodies, natural ligands of the receptor and anti-receptor antibodies, receptor anti-idiotypic antibodies, extraneous receptor and synthetic receptor mimics. The other type includes agents which inhibit viral entry, for example, when the virus attaches to and enters the host cell. For example, a number of "entry-inhibiting" or "entry-blocking" drugs are being developed to fight HIV, which targets the immune system white blood cells known as "helper T cells", and identifies these target cells through T-cell surface receptors designated "CRX4" and "CCR5". Thus, CRX4 and CCR5 receptor inhibitors such as amantadine and rimantadine, can be used to inhibit viral infection, such as HIV, influenza, and hepatitis B and C viral infections. Another entry-blocker is pleconaril, which works against rhinoviruses, which cause the common cold, by blocking a pocket on the surface of the virus that controls the uncoating process.

Further antiviral agents that can be used in combination with the inhibitory compounds described herein include agents which interfere with viral processes that synthesize virus components after a virus invades a cell. Representative agents include nucleotide and nucleoside analogues that look like the building blocks of RNA or DNA, but deactivate the enzymes that synthesize the RNA or DNA once the analogue is incorporated. Acyclovir is a nucleoside analogue, and is effective against herpes virus infections. Zidovudine (AZT), 3TC, FTC, and other nucleoside reverse transcriptase inhibitors (NRTI), as well as non-nucleoside reverse transcriptase inhibitors (NNRTI), can also be used. Integrase inhibitors can also be used.

Once a virus genome becomes operational in a host cell, it then generates messenger RNA (mRNA) molecules that direct the synthesis of viral proteins. Production of mRNA is initiated by proteins known as transcription factors, and certain active agents block attachment of transcription factors to viral DNA.

Other active agents include antisense oligonucleotides and ribozymes (enzymes which cut apart viral RNA or DNA at selected sites).

Some viruses, such as HIV, include protease enzymes, which cut viral protein chains apart so they can be assembled into their final configuration. Protease inhibitors are another type of antiviral agent that can be used in combination with the inhibitory compounds described herein.

The final stage in the life cycle of a virus is the release of completed viruses from the host cell. Some active agents, such as zanamivir (Relenza) and oseltamivir (Tamiflu) treat influenza by preventing the release of viral particles by blocking a molecule named neuraminidase that is found on the surface of flu viruses.

Still other active agents function by stimulating the patient's immune system. Interferons, including pegylated interferons, are representative compounds of this class. Interferon alpha is used, for example, to treat hepatitis B and C. Various antibodies, including monoclonal antibodies, can also be used to target viruses.

Any of the above-mentioned compounds can be used in combination therapy with the inhibitors described herein.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating viral infections, an effective amount of the inhibitory compound is an amount sufficient to suppress the growth and proliferation of the virus. Viral infections can be prevented, either initially, or from re-occurring, by administering the compounds described herein in a prophylactic manner. Preferably, the effective amount is sufficient to obtain the desired result, but insufficient to cause appreciable side effects.

The effective dose can vary, depending upon factors such as the condition of the patient, the severity of the viral infection, and the manner in which the pharmaceutical composition is administered. The effective dose of compounds will of course differ from patient to patient, but in general includes amounts starting where desired therapeutic effects occur but below the amount where significant side effects are observed.

The compounds, when employed in effective amounts in accordance with the method described herein, are effective at inhibiting the proliferation of certain viruses, but do not significantly effect normal cells.

For human patients, the effective dose of typical compounds generally requires administering the compound in an amount of at least about 1 mg, often at least about 10 mg, and frequently at least about 500 mg to 2 grams/24 hr/patient. The effective dose generally does not exceed about 2 g/patient/24 hr/patient, often does not exceed about 1000 mg/patient/24 hr/patient, and frequently does not exceed about 500 mg/patient/24 hr/patient.

V. Methods for Identifying an Inhibitor of Retroviral Propogation

The compounds described herein can be evaluated for their ability to inhibit viral propagation, for example, retroviral propagation, using the methods described herein. The retroviral propagation can be inhibited, for example, by a) inhibiting retroviral reverse transcription, b) inhibiting the binding of a host cell tRNA and a target nucleic acid molecule, c) inhibiting the viruses recruitment of the retroviral primer, human $tRNA^{Lys3}$, d) inhibiting HIV translation of viral RNA to precursor proteins, and/or e) inhibiting HIV's final packaging and assembly.

These individual methods for identifying inhibitors of retroviral propagation are discussed below.

Identifying Inhibitors of Retroviral Reverse Transcription

In one aspect, putative inhibitors of retroviral reverse transcription can be identified. In another aspect, putative inhibitors of tRNA's ability to bind to a target nucleic acid molecule can be identified. The identification can be done in a high through-put manner. Transfer RNA (tRNA) is involved in reverse transcription through the recognition of a corresponding site on the retroviral genome priming reverse transcription. Identifying inhibitors of reverse transcription may lead to the identification of therapeutic compounds for use in treating retroviral infection in a host cell.

The screening methods involve forming a mixture having a tRNA anticodon stem-loop (ASL) fragment, a target nucleic acid molecule that is capable of binding to the tRNA fragment, and a test compound. In one aspect, the target nucleic acid molecule corresponds to a fragment of the retroviral genome involved in reverse transcription. The resulting mixture is incubated under conditions that allow binding of the tRNA fragment and the target nucleic acid in the absence of the test compound. The method further involves detecting whether the test compound inhibits the binding of the tRNA fragment to the target nucleic acid, where the absence of binding of the tRNA ASL fragment and the target nucleic acid molecule is indicative of the test compound being an inhibitor of retroviral reverse transcription. In one aspect, the detection involves the use of labels to detect the inhibition of binding of the tRNA fragment to the target nucleic acid molecule.

Methods for Identifying Inhibitors of Binding of a Host Cell tRNA to a Target Nucleic Acid Molecule In another aspect, the ability of a putative inhibitor to bind a tRNA to a target nucleic acid molecule can be assayed. The assay involves forming a mixture containing a host cell tRNA ASL fragment, a target nucleic acid molecule that is capable of binding to the tRNA fragment, and a test compound. The resulting mixture is incubated under conditions that allow binding of the tRNA fragment and the target nucleic acid in the absence of the test compound. The method further involves detecting whether the test compound inhibits the binding of the tRNA fragment to the target nucleic acid, where binding of the tRNA ASL fragment and the target nucleic acid molecule is indicative of the test compound being an inhibitor of binding of a tRNA to a target nucleic acid molecule. In one aspect, the detection involves the use of labels to detect the inhibition of binding of the tRNA fragment to the target nucleic acid molecule.

Methods for Identifying Inhibitors of HIV Reverse Transcription (RT) Complex Formation In another aspect, the ability of a compound to function as an inhibitor of HIV reverse transcriptase (RT) complex formation can be assayed. The assay involves forming a mixture containing a tRNA ASL fragment, a target nucleic acid molecule capable of binding to the tRNA fragment, and a test compound. The resulting mixture is incubated under conditions that allow binding of the tRNA fragment and the target nucleic acid in the absence of the test compound. The method further involves detecting whether the test compound inhibits the binding of the tRNA fragment to the target nucleic acid. In one aspect, the detection involves the use of labels to detect the inhibition of binding of the tRNA fragment to the target nucleic acid molecule, where the inhibition indicates that the test compound is capable of inhibiting the formation of the RT complex.

In another aspect, the assay may involve detecting the binding of the putative inhibitor to either the tRNA fragment, the target nucleic acid, or both the tRNA fragment and the target nucleic acid. In one aspect, the binding of the putative inhibitor is indicative of the test compound being an inhibitor of retroviral propagation, retroviral infection, reverse transcription, or tRNA binding.

Methods for Identifying Inhibitors of Viral Recruitment of Human tRNA$^{Lys3}$.

In yet another aspect, the ability of a putative inhibitor to inhibit HIV's recruitment of the retroviral primer, human tRNA$^{Lys3}$ can be assayed. The assay involves forming a mixture comprising a linear sequence of a tRNA anticodon stem loop fragment that is not capable of forming a stem-loop, a target nucleic acid molecule capable of binding to the tRNA anticodon stem loop fragment, and a test compound, wherein the target nucleic acid molecule corresponds to a portion of a retroviral genome involved in recruitment of retroviral primer recruitment. The mixture is incubated under conditions that allow binding of the tRNA anticodon stem loop fragment and the target nucleic acid molecule in the absence of the test compound. One can then detect whether or not the test compound inhibits the binding of the tRNA anticodon stem loop fragment and the target nucleic acid molecule. The absence of binding of the tRNA ASL fragment and the target nucleic acid molecule is indicative of the test compound being an inhibitor retroviral primer recruitment.

Methods for Identifying Inhibitors of Viral RNA Translation

In still another aspect, the ability of a putative inhibitor of viral RNA translation to viral precursor proteins can be assayed. The assay involves forming a mixture comprising a linear sequence of a tRNA anticodon stem loop fragment that is not capable of forming a stem-loop, a target nucleic acid molecule capable of binding to the tRNA anticodon stem loop fragment, and a test compound; incubating the mixture under conditions that allow binding of the tRNA anticodon stem loop fragment and the target nucleic acid molecule in the absence of the test compound; and detecting whether or not the test compound inhibits the binding of the tRNA fragment and the target nucleic acid molecule where binding of the tRNA ASL fragment and the target nucleic acid molecule is indicative of the test compound being an inhibitor of tRNA recruitment during viral RNA translation to viral precursor proteins.

The inhibitors can inhibit the retroviral infection by inhibiting any step of a virus lifecycle, including, but not limited to, reverse transcription, viral assembly, RT complex formation, recruitment of the retroviral primer, human tRNA$^{Lys3}$, translation of viral RNA to precursor proteins, and the final packaging and assembly. Moreover, the inhibitors may inhibit retroviral infection, delay the infection, or slow the progression of the infection.

VI. tRNA Fragments Useful in the Methods Described Herein

The tRNA fragments (or "tool tRNA fragments") for use in the screening methods described herein can be a fragment from any tRNA. Specific tRNA fragments described in the formulas below are another aspect of the invention, and these fragments can be included in the kits described herein.

The tRNA fragments (or "tool tRNA fragments") for use in the methods of the present disclosure can be a fragment from any tRNA. The tRNA fragment may be obtained or derived from or corresponds to a tRNA$^{Ala}$, tRNA$^{Arg}$, tRNA$^{Asn}$, tRNA$^{Asp}$, tRNA$^{Cys}$, tRNA$^{Gln}$, tRNA$^{Glu}$, tRNA$^{Gly}$, tRNA$^{His}$, tRNA$^{Ile}$, tRNA$^{Leu}$, tRNA$^{Lys}$, tRNA$^{Met}$, tRNA$^{Phe}$, tRNA$^{Pro}$, tRNA$^{Ser}$, tRNA$^{Thr}$, tRNA$^{Trp}$, tRNA$^{Tyr}$, and tRNA$^{Val}$. In one aspect, the tRNA fragment corresponds to tRNA$^{Lys}$. In another aspect, the tRNA fragment is derived from or corresponds to the tRNA$^{Lys}$ anticodon stem loop (ASL). In another aspect, the tRNA fragment corresponds to a fragment of nucleotides 32-43 of the human tRNA$^{Lys}$. The position numbers used herein refer to the nucleotide position numbering of the conventional tRNA numbering as disclosed in Sprinzl, et al. *Nucl. Acids. Res.*, 26, 148-153 (1998). In one aspect, the tRNA fragment is a fragment from a host cell tRNA, such as a mammalian host cell, including, but not limited to, human, feline, and simian host cells.

The tRNA fragments may incorporate one or more modified nucleosides. In one aspect, the tRNA fragment incorporates one, two, three, or more modified nucleosides into the nucleic acid sequence. In another aspect, the tRNA fragments incorporate three modified nucleosides into the tRNA fragment nucleic acid molecules. Modified nucleosides that can be incorporated into the tRNA fragments include any modified nucleotide, including, but not limited to unknown modified adenosine (?A), 1-methyladenosine (m1A), 2-methyladenosine (m2A), $N^6$-isopentenyladenosine (i6A), 2-methylthio-$N^6$-isopentenyladenosine (ms2i6A), $N^6$-methyladenosine (m6A), $N^6$-threonylcarbamoyladenosine (t6A), $N^6$-methyl-$N^6$ threonylcarbomoyladenosine (m6t6A), 2-methylthio-$N^6$-threonylcarbamoyladenosine (ms2t6A), 2'-O-methyladenosine I Inosine (Am), 1-methylinosine Ar(p) 2'-O-(5-phospho)ribosyladenosine (m1I), $N^6$-(cis-hydroxyisopentenyl)adenosine (io6A), Unknown modified cytidine (?C), 2-thiocytidine (s2C), 2'-O-methylcytidine (Cm), $N^4$-acetylcytidine (ac4C), 5-methylcytidine (m5C), 3-methylcytidine (m3C), lysidine (k2C), 5-formylcytidin (f5C), 2'-O-methyl-5-formylcytidin (f5 Cm), unknown modified guanosine (?G), 2'-O-(5phospho) ribosylguanosine (Gr(p)), 1-methylguanosine (m1G), $N^2$-methylguanosine (m2G), 2'-O-methylguanosine (Gm), $N^2N^2$-dimethylguanosine (m22G), $N^2,N^2,2'$-O-trimethylguanosine (m22Gm), 7-methylguanosine (m7G), archaeosine (fa7d7G), queuosine (Q), mannosyl-queuosine (manQ), galactosyl-queuosine (galQ), wybutosine (yW), peroxywybutosine (02yW), unknown modified uridine (?U), 5-methylaminomethyluridine (mnm5U), 2-thiouridine (s2U), 2'-O-methyluridine (Um), 4-thiouridine (s4U), 5carbamoylmethyluridine (ncm5U), 5-methoxycarbonylmethyluridine (mcm5U), 5methylaminomethyl-2-thiouridine (mnm5s2U), 5-methoxycarbonylmethyl-2-thiouridine (mcm5s2U), uridine 5-oxyacetic acid (cmo5U), 5-methoxyuridine (mo5U), 5 carboxymethylaminomethyluridine (cmnm5U), 5-carboxymethylaminomethyl-2-thiouridine (cmnm5s2U), 3-(3-amino-3-carboxypropyl)uridine (acp3U), 5-(carboxyhydroxymethyl)uridinemethyl ester (mchm5U), 5-carboxymethylaminomethyl-2'-O-methyluridine (cmnm5Um), 5-carbamoylmethyl-2'-O-methyluridine (ncm5Um), Dihydrouridine (D), pseudouridine (ψ), 1-methylpseudouridine (m1ψ), 2'-O-methylpseudouridine (ψm), ribosylthymine (m5U), 5-methyl-2-thiouridine (m5s2U), and 5,2'-O-dimethyluridine (m5Um).

In a preferred aspect, the fragment tRNA contains modified nucleic acids corresponding to positions 34, 37, and 39 in the anticodon stem loop of a tRNA. The position numbers used herein refer to the nucleotide position numbering of the conventional tRNA numbering as disclosed in Sprinzl, et al. *Nucl. Acids. Res.*, 26, 148-153 (1998). In one aspect, the tRNA fragment comprises, or consists of, a molecule having the sequence 5'-GCUXUUAYZCUG, in which the X, Y, and Z refer to modified or unmodified nucleosides. In one aspect, the X, Y, and Z refer to modified nucleosides, such as mnm5s2U, mcm5s2U, ms2t6A, s2U, ψ, and t6A. In another aspect, the tRNA fragment has the nucleic acid sequence 5'-CU(mnm5s2U)UU(ms2t6A)A(ψ)CUGC. In another aspect, the tRNA fragment has the nucleic acid sequence 5'-GCU(mnm5s2U)UU(ms2t6A)A(ψ)CUG.

The tRNA fragment may correspond to any portion of the tRNA involved in propagation of the retrovirus through binding, directly or indirectly, to the retroviral genome. In a preferred aspect, the tRNA fragment corresponds to the anticodon stem loop (ASL) of the tRNA.

The tRNA fragment may correspond to any portion of the host cell's tRNA involved in nucleotide binding, such as involvement in the reverse transcription (RT) complex formation. For example, the tRNA may be involved in binding to a retroviral genome to initiate, prime, or facilitate reverse transcription of the retroviral genome. In one aspect, the fragment tRNA corresponds to a fragment of the anticodon stem loop of any tRNA. In one aspect, the fragment corresponds to a fragment from the anticodon stem loop of tRNA$^{-Lys}$. In another aspect, the tRNA fragment corresponds to a fragment from the anticodon stem loop of human tRNA$^{-Lys}$. In another aspect, the tRNA fragment corresponds to a fragment from nucleotides 32-43 of human tRNA$^{.Lys3}$.

The tRNA fragment may also be any length of a fragment from a tRNA. In one aspect, the tRNA fragment comprises a fragment of between 9 to 15 continuous nucleotides of a tRNA, 10 to 14 continuous nucleotides of a tRNA, or between 11 to 13 continuous nucleotides of a tRNA. In another aspect, the fragment is a fragment of 8, 9, 10, 11, 12, 13, 14, 15, or 16 continuous nucleotides of a tRNA. In a further aspect, the fragment is a fragment of 12 continuous nucleotides of a tRNA.

The tRNA fragment may or may not be capable of forming a secondary structure. In a one aspect, the tRNA fragment is not capable of forming a stem loop structure with itself. In another aspect, the fragment is a linear fragment of a tRNA that is not capable of forming a stem loop structure with itself.

The tRNA fragment may also be linked to additional nucleic acids. For example, the tRNA fragment may be linked to one or more additional nucleic acids depending on the assay method. In one aspect, the tRNA fragment may be linked to nucleotides used to attach the fragment to a solid support surface. In another aspect, the fragment tRNA is linked to additional nucleic acid molecules at one or both terminal end of the tRNA fragment. In another aspect, the fragment tRNA is linked to additional nucleic acid molecules at both terminal ends. The additional nucleic acid sequences can be any length, preferably between 8 and 16 nucleotides, between 10 and 14 nucleotides, more preferably 12 nucleotides in length. In one aspect, the terminal sequences do not allow the tRNA fragment to form a secondary structure, such as a hairpin loop structure.

A target nucleic acid molecule may correspond to any nucleic acid molecule, such as a DNA or an RNA molecule that is involved in retroviral propagation or retroviral reverse transcription. In one aspect, the target nucleic acid molecule corresponds to any nucleic acid molecule that is capable of binding to the tRNA fragment and is involved in retroviral propagation or reverse transcription. In another aspect, the target nucleic acid molecule corresponds to a nucleic acid molecule involved in reverse transcription of a retroviral genome. In another aspect, the target nucleic acid molecule corresponds to ribonucleic acid from a retroviral genome. In another aspect, the target nucleic acid molecule corresponds to a nucleic acid molecule that is involved in priming retroviral reverse transcription.

The target nucleic acid molecule may be any length and may include the entire retroviral genome and fragments thereof. In one aspect, the target nucleic acid molecule includes any fragment of a retroviral genome involved in tRNA binding, and includes fragments of at least 5, 6, 7, 8, 9, 10, 11, 12, 13, 14, 15, 20, 25, 30, 35, 40, 45, 50 or more nucleotides. In another aspect, the target nucleic acid is about the same, or is the same length as the tool tRNA fragment.

In another aspect, the target nucleic acid molecule corresponds to a nucleic acid molecule from a Human Immunodeficiency Virus (HIV), such as HIV-1 or HIV-2. In another aspect, the target molecule corresponds to HIV-1. In another aspect, the target nucleic acid molecule corresponds to a nucleic acid molecule involved in priming HIV reverse transcription.

Such target nucleic acid molecules can be derived from or correspond to any portion of the HIV genome involved in reverse transcription through the binding or association with a host cell tRNA. In one aspect, the target nucleic acid molecule is derived from or corresponds to the 5' untranslated region of the HIV genome. In another aspect, the target nucleic acid molecule corresponds to a fragment including residues 157 to 169 of the 5' untranslated region of HIV-1. The target nucleic acid sequence may be complementary to the tRNA fragment. In a one aspect, the target nucleic acid molecule comprises the nucleic acid sequence 5'-GCGGU-GUAAAAG.

Specific Isolated tRNA Fragments

In one aspect, the isolated tRNA fragment comprises the sequence 5'-GCUXUUAYZCUG, in which the X, Y, and Z refer to modified nucleosides.

Representative modified nucleosides include unknown modified adenosine (?A), 1-methyladenosine (m1A), 2-methyladenosine (m2A), $N^6$-isopentenyladenosine (i6A), 2-methylthio-$N^6$-isopentenyladenosine (ms2i6A), $N^6$-methyladenosine (m6A), $N^6$-threonylcarbamoyladenosine (t6A), $N^6$-methyl-$N^6$ threonylcarbomoyladenosine (m6t6A), 2-methylthio-$N^6$-threonylcarbamoyladenosine (ms2t6A), 2'-O-methyladenosine I Inosine (Am), 1-methylinosine Ar(p) 2'-O-(5-phospho)ribosyladenosine (m1I), $N^6$-(cis-hydroxyisopentenyl)adenosine (io6A), Unknown modified cytidine (?C), 2-thiocytidine (s2C), 2'-O-methylcytidine (Cm), $N^4$-acetylcytidine (ac4C), 5-methylcytidine (m5C), 3-methylcytidine (m3C), lysidine (k2C), 5-formylcytidin (f5C), 2'-O-methyl-5-formylcytidin (f5 Cm), unknown modified guanosine (?G), 2'-O-(5phospho) ribosylguanosine (Gr(p)), 1-methylguanosine (m1G), $N^2$-methylguanosine (m2G), 2'-O-methylguanosine (Gm), $N^2N^2$-dimethylguanosine (m22G), $N^2,N^2$,2'-O-trimethylguanosine (m22Gm), 7-methylguanosine (m7G), archaeosine (fa7d7G), queuosine (Q), mannosyl-queuosine (manQ), galactosyl-queuosine (galQ), wybutosine (yW), peroxywybutosine (02yW), unknown modified uridine (?U), 5-methylaminomethyluridine (mnm5U), 2-thiouridine (s2U), 2'-O-methyluridine (Um), 4-thiouridine (s4U), 5carbamoylmethyluridine (ncm5U), 5-methoxycarbonylmethyluridine (mcm5U), 5methylaminomethyl-2-thiouridine (mnm5s2U), 5-methoxycarbonylmethyl-2-thiouridine (mcm5s2U), uridine 5-oxyacetic acid (cmo5U), 5-methoxyuridine (mo5U), 5 carboxymethylaminomethyluridine (cmnm5U), 5-carboxymethylaminomethyl-2-thiouridine (cmnm5s2U), 3-(3-amino-3-carboxypropyl)uridine (acp3U), 5-(carboxyhydroxymethyl)uridinemethyl ester (mchm5U), 5-carboxymethylaminomethyl-2'-O-methyluridine (cmnm5Um), 5-carbamoylmethyl-2'-O-methyluridine (ncm5Um), Dihydrouridine (D), pseudouridine (ψ), 1-methylpseudouridine (m1ψ), 2'-O-methylpseudouridine (ψm), ribosylthymine (m5U), 5-methyl-2-thiouridine (m5s2U), and 5,2'-O-dimethyluridine (m5Um).

In one embodiment, the modified nucleosides are mnm5s2U, mcm5s2U, ms2t6A, s2U, ψ, or t6A.

One specific tRNA fragment comprises the nucleic acid sequence 5'-CU(mnm5 s2U)UU(ms2t6A)A('1')CUGC.

Another specific tRNA fragment comprises the nucleic acid sequence 5'-GCU(mnm5 s2U)UU(ms2t6A)A('1') CUG.

Any of these tRNA fragments can further comprise a label. The label can be detectable, either directly or indirectly, by spectroscopic, photochemical, biochemical, immunochemical, or chemical means.

Representative labels include radioactive isotopes (for example, $^{32}P$, $^{35}S$, and $^3H$), dyes, fluorescent dyes (for example, Cy5 and Cy3), fluorophores (for example, fluorescein), electron-dense reagents, enzymes and their substrates (for example, as commonly used in enzyme-linked immunoassays, such as, alkaline phosphatase and horse radish peroxidase), biotin-streptavidin, digoxigenin, or hapten; and proteins for which antisera or monoclonal antibodies are available. The label can also be an "affinity tag."

Where the label comprises an affinity tag, the isolated tRNA fragments can be captured with a complimentary ligand coupled to a solid support that allows for the capture of the affinity tag-labeled tRNA fragment. Representative affinity tags and complimentary partners include biotin-streptavidin, complimentary nucleic acid fragments (for example, oligo dT-oligo dA, oligo T-oligo A, oligo dO-oligo dC, oligo O-oligo C), aptamers, or haptens and proteins for which antisera or monoclonal antibodies are available.

When a biological interaction brings the beads together, a cascade of chemical reactions acts to produce a greatly amplified signal. On laser excitation, a photosensitizer in the "Donor" bead converts ambient oxygen to a more excited singlet state. The singlet state oxygen molecules diffuse across to react with a thioxene derivative in the Acceptor bead generating chemiluminescence at 370 nm that further activates fluorophores contained in the same bead. The fluorophores subsequently emit light at 520-620 nm.

In one example of a commercially-available alpha bead, the Donor beads comprise biotin or are directly bound to RNA. The Acceptor beads include a His6 tag, hemagglutinin (HA), digoxin/digoxigenin (DIG), or fluorescein (FITC).

VII. Synthetic Methods for Producing Isolated Ribonucleotides

A variety of methods are known in the art for making nucleic acids having a particular sequence or that contain particular nucleic acid bases, sugars, internucleoside linkages, chemical moieties, and other compositions and characteristics. Anyone or any combination of these methods can be used to make a nucleic acid, polynucleotide, or oligonucleotide for the present invention. Said methods include, but are not limited to: (1) chemical synthesis (usually, but not always, using a nucleic acid synthesizer instrument); (2) post-synthesis chemical modification or derivatization; (3) cloning of a naturally occurring or synthetic nucleic acid in a nucleic acid cloning vector (e.g., see Sambrook, et aI., Molecular Cloning: A Laboratory Approach 2nd ed., Cold Spring Harbor Laboratory Press, 1989) such as, but not limited to a plasmid, bacteriophage (e.g., mB or lamda), phagemid, cosmid, fosmid, YAC, or BAC cloning vector, including vectors for producing single-stranded DNA; (4) primer extension using an enzyme with DNA template-dependent DNA polymerase activity, such as, but not limited to, Klenow, T4, T7, rBst, Taq, Tfl, or Tth DNA polymerases, including mutated, truncated (e.g., exo-minus), or chemically-modified forms of such enzymes; (5) PCR (e.g., see Dieffenbach, C. W., and Dveksler, eds., PCR Primer: A Laboratory Manual, 1995, Cold Spring Harbor Laboratory Press, Cold Spring Harbor, N.Y.); (6) reverse transcription (including both isothermal synthesis and RT-PCR) using an enzyme with reverse transcriptase activity, such as, but not limited to, reverse transcriptases derived from avian myeloblasosis virus (AMV), Maloney murine leukemia virus (MMLV), *Bacillus stearothermophilus* (rBst), *Thermus thermophilus* (Tth); (7) in vitro transcription using an enzyme with RNA polymerase activity, such as, but not limited to, SP6, T3, or T7 RNA polymerase, Tth RNA polymerase, *E. coli* RNA polymerase, or another enzyme; (8) use of restriction enzymes and/or modifying enzymes, including, but not limited to exo- or endonucleases, kinases, ligases, phosphatases, methylases, glycosylases, terminal transferases, including kits containing such modifying enzymes and other reagents for making particular modifications in nucleic acids; (9) use of polynucleotide phosphorylases to make new randomized nucleic acids; (10) other compositions, such as, but not limited to, a ribozyme ligase to join RNA molecules; and/or (11) any combination of any of the above or other techniques known in the art. Oligonucleotides and polynucleotides, including chimeric (i.e., composite) molecules and oligonucleotides with non-naturally-occurring bases, sugars, and internucleoside linkages are commercially available (e.g., see the 2000 Product and Service Catalog, TriLink Biotechnologies, San Diego, Calif., USA)

The tRNA fragment or the target nucleic acid, or both the tRNA fragment and the target nucleic acid molecule may be detectably labeled to facilitate detection. In a preferred aspect, the tRNA fragment is labeled with a fluorophore to facilitate detection. In another aspect, the target nucleic acid molecule is labeled with biotin to facilitate detection. In another preferred aspect, the tRNA fragment is labeled with a fluorophore and the target nucleic acid molecule is labeled with biotin.

The tRNA fragment and target nucleic acid molecule may be labeled, for example, at either the 5' terminus, the 3'-terminus, or combinations of the 5'-terminus and the 3'terminus to facilitate detection. In addition, the test compound may also be labeled. In another embodiment, the tRNA fragment and the target nucleic acid molecule may have a detectable label attached to an internal position of the molecule to facilitate detection.

VIII. Methods for Detecting Binding (or Inhibition Thereof) of Target RNA to tRNA The methods for detecting binding of the target RNA to the tRNA or the inhibition of such binding may be performed using any method for such detection. For example, the AlphaScreen® assay (Packard Instrument Company, Meriden, Conn.). AlphaScreen® technology is an "Amplified Luminescent Proximity Homogeneous Assay" method utilizing latex microbeads (250 nm diameter) containing a photosensitizer (donor beads), or chemiluminescent groups and fluorescent acceptor molecules (acceptor beads). Upon illumination with laser light at 680 nm, the photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity to the donor bead (i.e., by virtue of the interaction of the target RNA and tRNA fragment), the singlet-state oxygen molecules reacts with chemiluminescent groups in the acceptor beads, which immediately transfer energy to fluorescent acceptors in the same bead. These fluorescent acceptors shift the emission wavelength to 520-620 nm, resulting in a detectable signal. Antagonists of the interaction of the target RNA with the tRNA fragment will thus inhibit the shift in emission wavelength, whereas agonists of this interaction would enhance it.

The disclosed methods may be performed by mixing the component nucleotide (e.g. the tool tRNA and the target RNA) and the test compound in any order, or simultaneously. For example, a target RNA may be first combined with a test compound to form a first mixture, and then a tool tRNA fragment may be added to form a second mixture. In another example, a target RNA, a tool tRNA and the test compound may all be mixed at the same time before incubation. In one aspect, the mixture is incubated under conditions that allow binding of the tRNA fragment and the target nucleic acid in the absence of the test compound.

The inhibition of binding of the tRNA fragment and the target nucleic acid molecule by the test compound may be detected using any method available for the detection of inhibition. In one aspect, the determining step may be performed using methods including, but not limited to, gel shift assays, chemical and enzymatic footprinting, circular dichroism and NMR spectroscopy, equilibrium dialysis, or in any of the binding detection mechanisms commonly employed with combinatorial libraries of probes or test compounds. The inhibition of binding indicates that the test compound may be useful for inhibiting propagation of the virus in the host.

The invention will be further explained by the following illustrative examples, which are intended to be non-limiting.

EXAMPLES

Example 1 Synthesis of Linear tRNA Anticodon Stem Loop Sequences

The first step in producing the fragment tRNA anticodon stem loop (ASL) sequences is the synthesis of the modified nucleotides, also known as phosphoramidites (Agris et. al *Biochimie.* (1995) 77(1-2):125-34). The modified nucleotides are then used during the synthesis of the RNA oligomers (Ogilvie et. al. *Proc Natl Acad Sci USA.* (1988) 85:5764-8). Synthetic approaches overcome the substantial barrier of obtaining sufficient amounts of natural products for the functional characterization studies. In addition to providing the fully modified ASL for characterization of the fragment tRNA:target nucleotide binding, the synthetic approach allows for the preparation of intermediate steps/forms of the modified material that can further elucidate the individual contribution of each modification step in enhanced tRNA binding.

Modified base nucleic acid molecules were prepared using a combination of methods for the synthesis, incorporation, and purification of all the modified nucleotides found in the $ASL^{Lys3}$ human tRNA. Modified base phosphoramidites were prepared using known methods, such as those disclosed in Ogilive et. aI, 1988. The $ASL^{Lys3}$ contains 3 modified bases denoted as mcm5s2U, ms2t6A and pseudouridine. Synthesis of the phosphoramides needed for the preparation of the synthetic mimics is described below in detail. Protocols for the polymers synthesis follow those developed for automated RNA synthesis (Ogilive et. al., 1988) with variations specific to the synthesis of the $ASL^{Lys3}$ mimics described below. The description includes methods for the removal of protection group required for automated synthesis and purification of the final products used in the assay.

The protecting group is subsequently removed after synthesis of the RNA oligomer. The addition of a protecting group to each modified base and ribose is described. While 2 position thio-groups can be oxidized in standard RNA synthesis protocols this has been overcome by using the tert-butyl hydroperoxide (10% solution in acetonitrile) oxidizing agent (Kumar and Davis, 1997). These synthetic RNA oligomers have been used in both functional (Yarian 2002 and Phelps 2004) and structural studies (Stuart 2000 and Murphy 2004).

Example IA: The Synthesis of the Protected Monomer Phosphoramidites mcm5s2U

The mcm5s2U nucleoside was prepared following published methods (Reese and Sanghvi 1984). Briefly, 2 thio-uridine was heated with 5 molar equivalents each of pyrrolidine and formaldehyde in aqueous solution for 1 h, under reflux, resulting in 2',3'-0isopropylidene-5-pyrrolidinomethyl-2-thiouridine. This base was subsequently treated with 10 molar equivalents of methyl iodide in acetonitrile at room temperature. After 16 hours, the products were concentrated under reduced pressure to give the putative methiodide which was then dissolved in acetonitrile and allowed to react with 3 molar equivalents of glycine t-butyl ester' at room temperature for 16 h. This product was then purified and protection of the ribose and phosphitylation follow the general scheme described below.

ms2t6A

The monomer was obtained by condensation of the 2',3', 5'-O-triacetyl derivative of ms2A with the isocyanate derived from L-threonine-O-t-butyldimethylsilyl (TBDMS)-pnitrophenylethyl ester, under conditions which eliminate racemization of the amino acid. The product was selectively deprotected at the sugar moiety. Standard procedures were employed for final protection of the 5'-O— and 2'-O-functions with dimethoxytrityl (DMTr) and with TBDMS groups, respectively, as well as for 3'-O-phosphitylation (Agris et al., 1995).

S2U

The thio group was not protected in this synthesis. Protection of the ribose and phosphitylation follow the general scheme in panel C of FIG. 1. Protection of the ribose and phosphitylation follow the general scheme described below.

The sugar-protected phenyl carbamate 6 of t6A nucleoside was synthesized from 1-O-acetyl-2,3,5-tri-O-benzoylribofuranose The carbamate was treated with L-threonine to furnish the sugar-protected t6A nucleoside using the method of Hong and Chheda. The remaining synthetic transformations followed general scheme described below.

Example IB: General Procedure for Ribose Protection and Phosphitylation

Methods for the protection of the modified nucleotide bases prior to synthesis of the RNA oligomer are provided (FIG. 1). Panel A of FIG. 1 illustrates protection with trifluoryl acetic acid. Panel B illustrates protection with benzoyl, and panel C illustrates the general protection of the ribose hydroxyl groups.

After base protection the scheme for the synthesis of 5'-O-(4,4'-dimethoxytrityl)-2'-O-tertbutyidimethylsilyi-modified ribonucleoside-3'-O-(2-cyanoethyl-N-diisopropyl) phosphoramidites is the same for both modified nucleotides (Panel C, FIG. 1). The protected nucleoside was dried by co-evaporation twice with pyridine and dissolved in pyridine. Tert-butyldimethylchlorosilane and imidazole were added and reacted for 4 hours at room temperature. The excess silyl chloride was decomposed with water and dichloromethane. The aqueous layer was extracted twice with dichloromethane and combined with the organic layer. The solvent was evaporated by vacuum yielding a gum which is then dissolved in ether and precipitated by pouring slowly into petroleum ether (4060° C.) with stirring. The precipitate was collected and washed twice with petroleum ether. At this point the crude product contains three components; the 2',3' disilylated, 2' silylated (major product) and 3' silylated isomers. The pure 2' protected isomer was purified by silica gel column chromatography. This product is then ready for phosphitylation.

The N-protected-5'-O-dimethoxytrityl-2'-O-tert-butyldimethylsilylribonucleosides were dried by two co-evaporations with anhydrous pyridine and THF. The residue was then dissolved in anhydrous THF under argon. Dimethylaminopyridine, N,N,N-ethyldiisopropylamine and cyano-ethoxydiisopropy amino-chlorophosphine were added through a rubber septum. After 2 hours the reaction mixture, was quenched with ethyl acetate and washed with 5% sodium bicarbonate followed by water. Aqueous washes were back extracted with ethyl acetate. Combined organic layers were dried over sodium sulphate. Solvent was evaporated yielding a viscous oil. The product was co-evaporated twice with toluene and the pale yellow phosphoramidite products were purified by flash silica gel chromatography.

Example IC: Protocols for the Synthesis of the Modified RNA Polymers

The synthesis of the RNA followed standard protocols for a 1 mol scale by solid phase b-cyanoethyl phosphoramidite chemistry with 2'-OTBDMS protection (Usman et al., 1987), and N-4-tbutyl phenoxyacetyl (tac) protection of A, G and C monomers (Sinha et al., 1993). A, G, C and U monomers with tac and 2'-O-TBDMS protection and rC(tac)-succinyl controlled pore glass (CPG) support with the following variations. Addition of the unmodified A, C, G and U monomers were coupled in 5-fold molar excess for 6 min in the presence of 0.3 M 5-(benzylthio)-IH-tetrazole in acetonitrile (Welz and Muller, 2002), whereas mcm5s2U and ms2t6A monomers were used in 3-fold excess and coupled for 10 min. Following the coupling, a 2 min capping was performed with tac anhydride and then a 3 min oxidation with 1M cumene hydroperoxide in toluene. At the end of the synthesis the 5'dimethoxytrityl group was left in place.

Example ID: Protocols for the Deprotection of the Intermediates

The deprotection of the RNA was carried out in 3 steps as follows. The argon dried CPG carrying the fully protected RNA was treated with 20 ml of absolutely anhydrous 10% 1,8-diazabicyclo[5.4.0]undec-7-ene (DBU) in tetrahydrofuran for 45 min at 45° C. to be eliminate the p-nitrophenylethyl and 2-cyanoethyl protecting groups. The supernatant was removed under a blanket of argon and the CPG was washed twice with dry THF. The CPG carrying partially deprotected RNA was then treated with 20 ml of 10% DBU in dry methanol under argon for 18 h at room temperature to cleave the nucleobase protecting groups and cleave the RNA from the CPG. The supernatant and methanol washings were dried in a Speedvac in a Falcon tube and then dried for 3 days in high vacuum (10)3 Torr) over phosphorus pentaoxide to remove the residual DBU. The 2'-O-TBDMS protected RNA was desilylated using 12 ml of triethylamine trihydrofluoride (Gasparutto et al., 1992) with vigorous stirring during 24 h at room temperature. During this step the DMT group is also removed from the 5'-terminal G residue. The reaction was quenched by addition of sterile water (1.2 ml) and the crude RNA was precipitated with butanol and kept at 20° C. for 24 h to complete the precipitation. The RNA was collected by centrifugation, washed with butanol.

Example IE: Purification of the RNA Polymers

The synthetic RNA polymer products are purified by HPLC. The deprotected material is desalted using C18 SEP-PAK and purified by preparative anion-exchange HPLC using a gradient of sodium chloride. In some cases additional purification is required using reverse phase chromatography. To assure that the polymer product is correct it is analyzed by electrospray mass spectroscopy and nucleoside composition analysis.

Example II. Inhibitor Screening Assay

Figure 3:
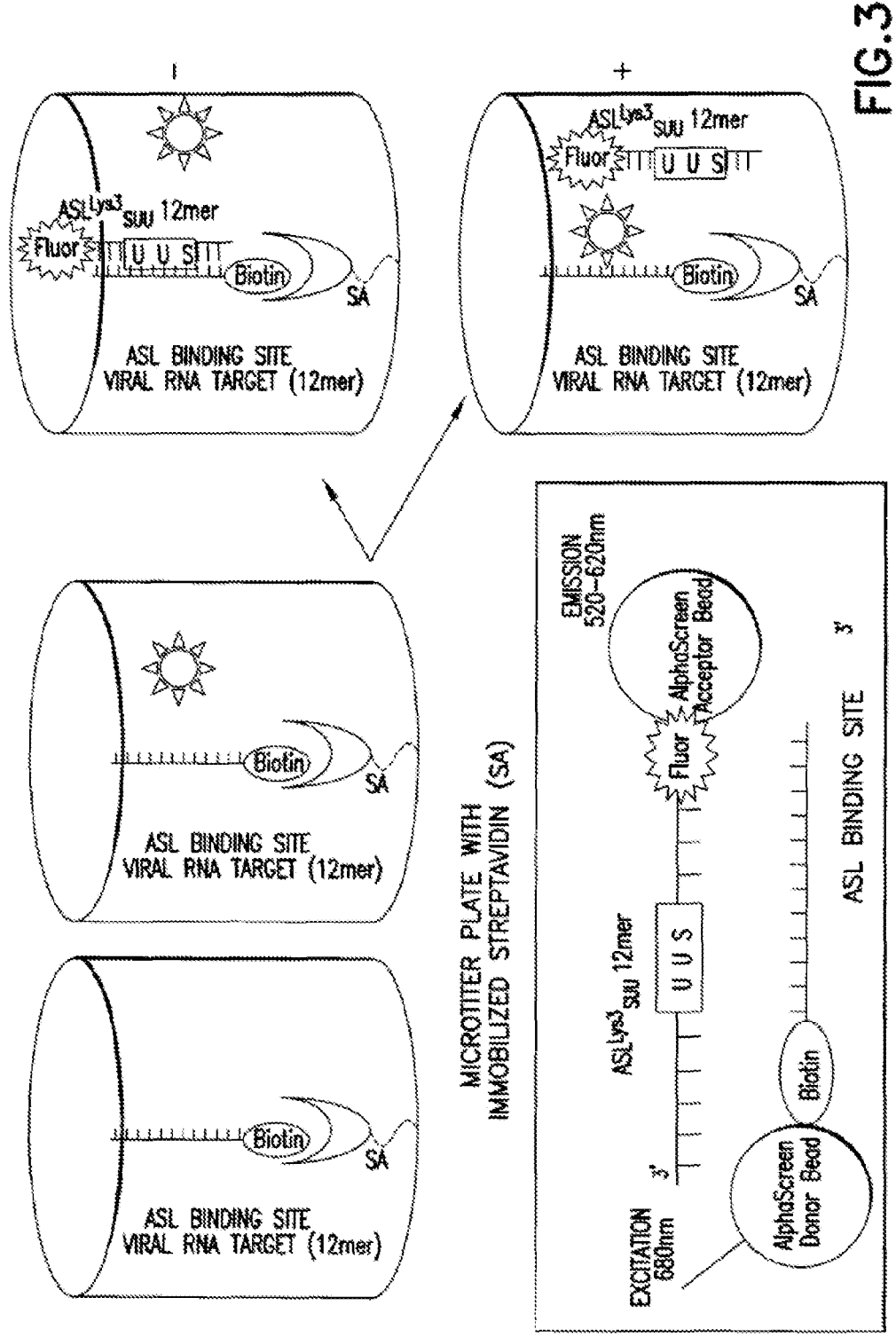
FIG. 3 provides a comparison of one example of an immobilized assay and an assay using the AlphaScreen™ assay.
Figure 4A:
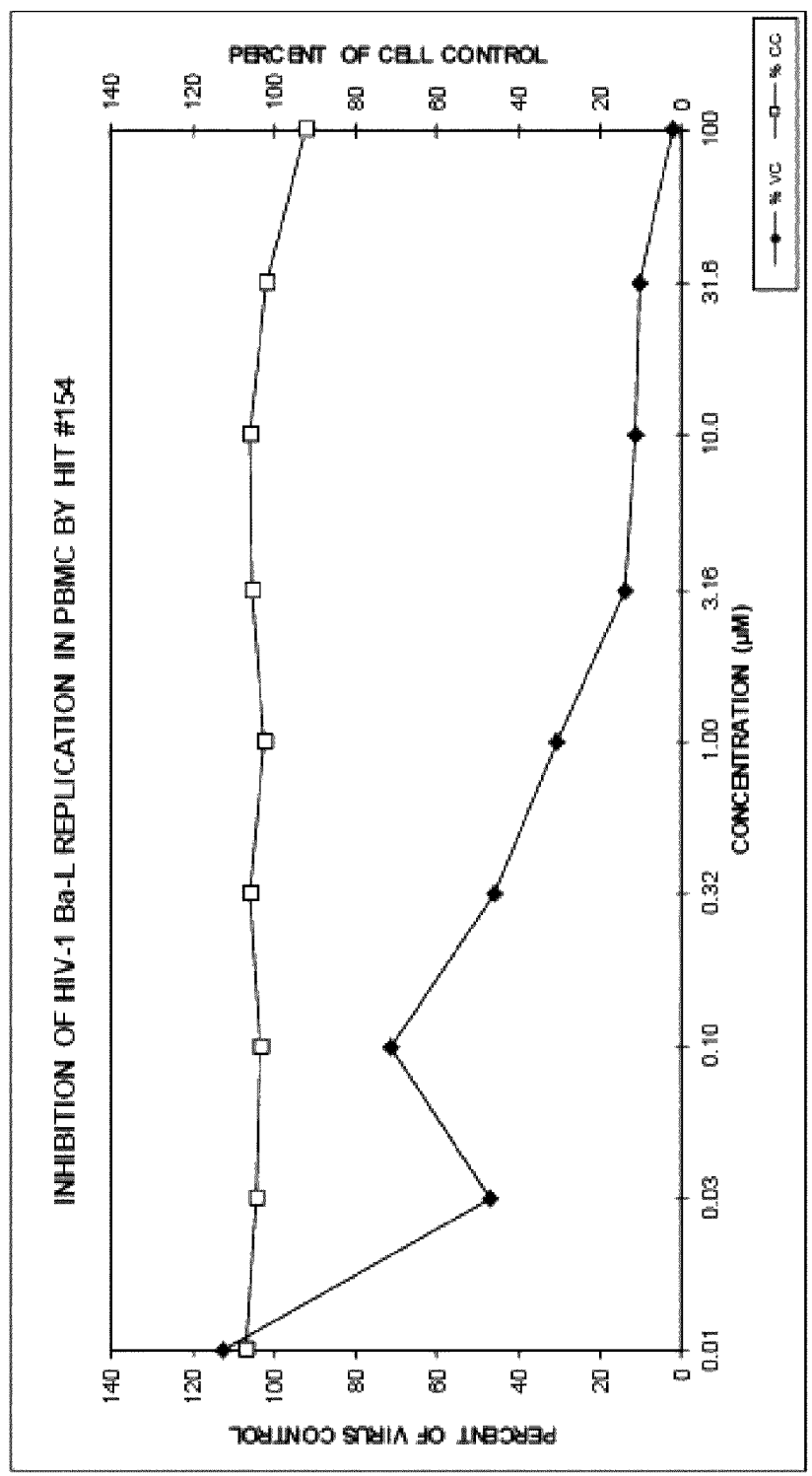
FIGS. 4A-B and 5A-B are charts summarizing data obtained for two compounds using an example of the HIV assay, versus a control.
Figure 4B:
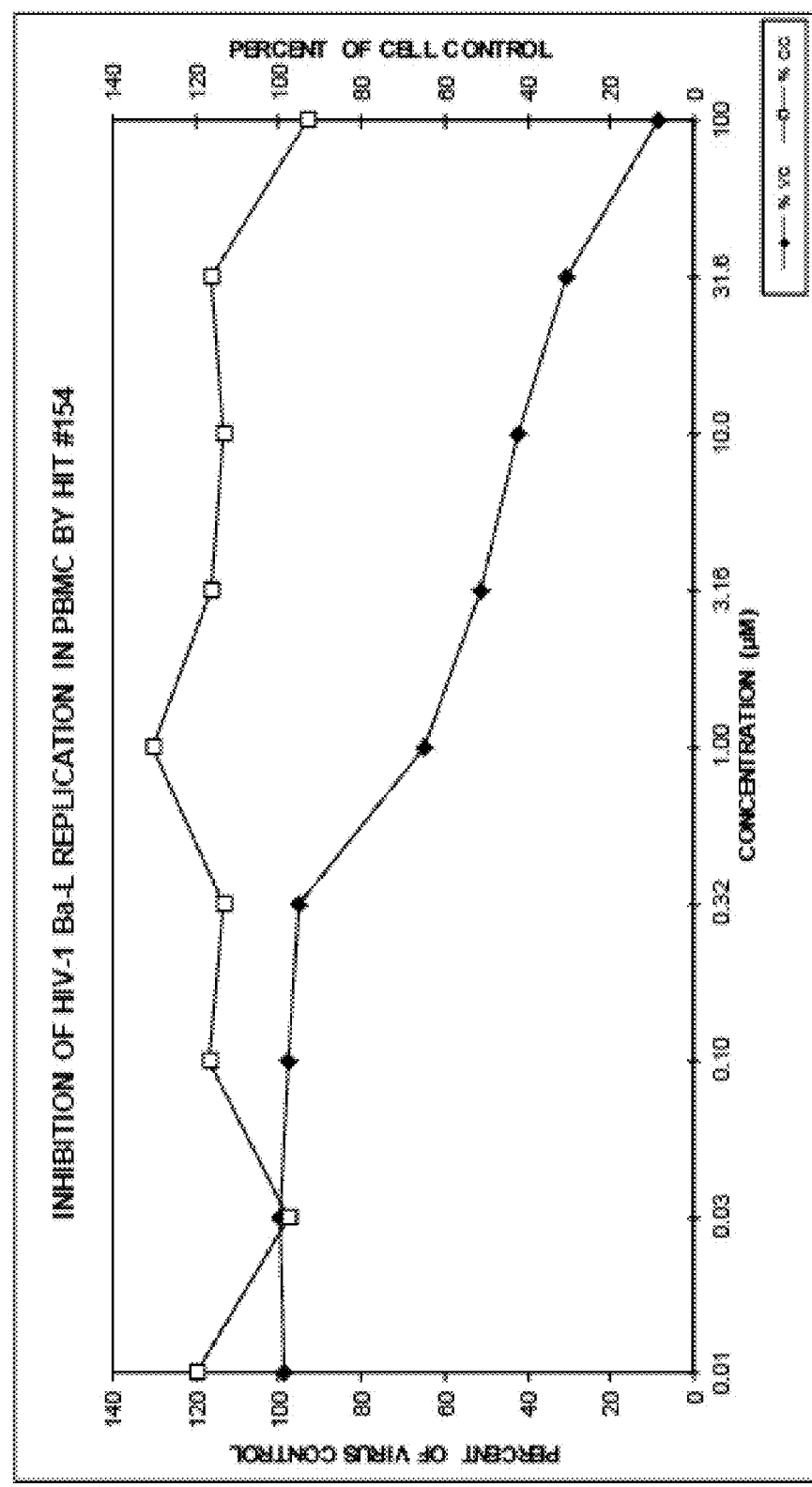
Figure 5A:
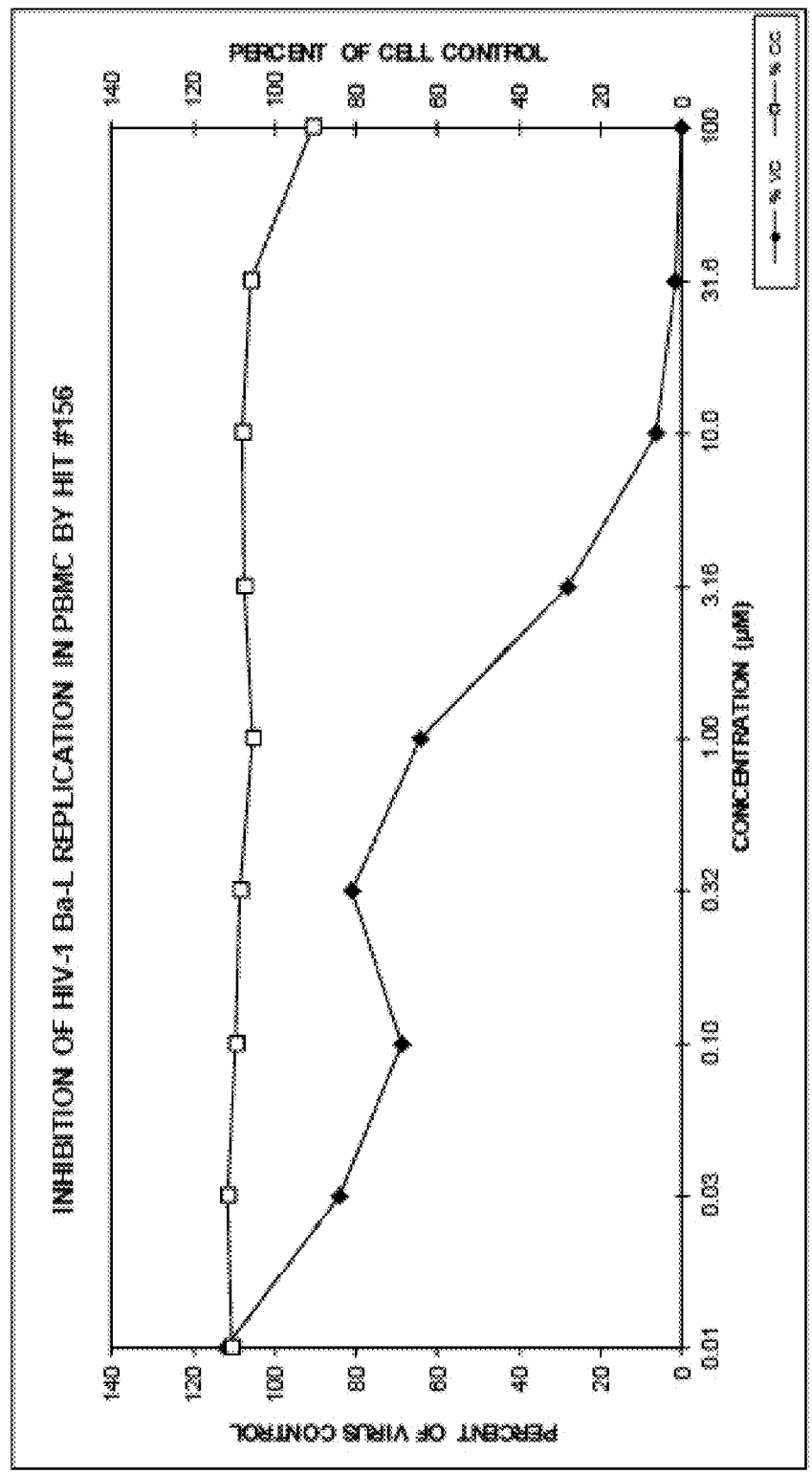
Figure 5B:
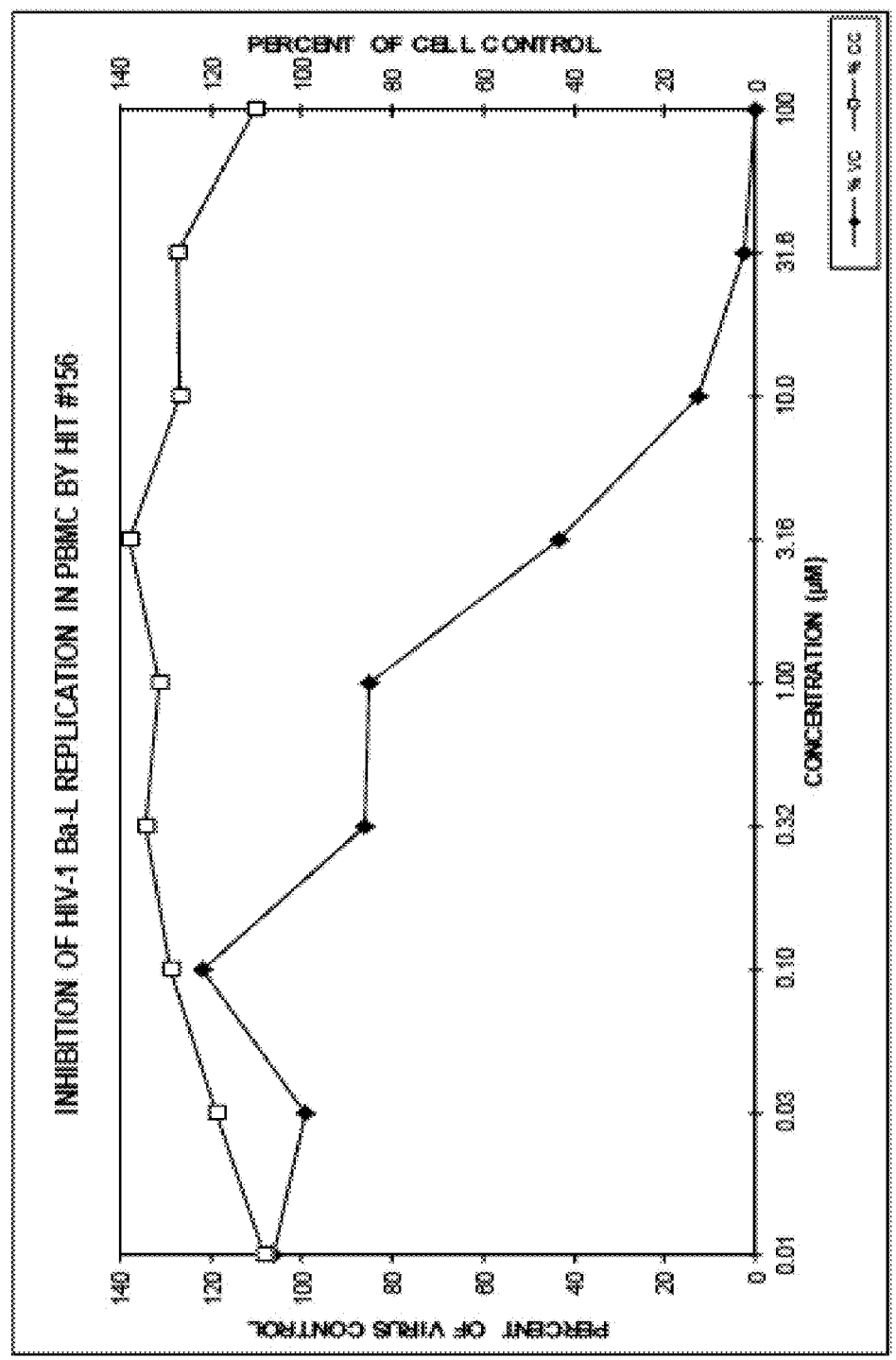

Two assays were developed using tool and target RNAs, the immobilized assay and the Alphascreen assay (FIG. 3). Both assays use the same two RNA components (the target RNA and the tRNA fragment). In the example, the HIV viral RNA target is a 12mer with a 3' Biotin, while the Human tRNA mimic is a synthetic 12mer containing the native modified nucleotides and 3' fluorescein. These two RNAs mimic an essential complex of the HIV replication complex.

As set forth more fully below, the immobilization assay uses a three step process that first involves the binding of the target RNA to an avidin coated microtiter plate. Then, the test compound (drug/small molecule), denoted as a star, is incubated with the target sequence for 30 min. Then, the tRNA mimic was added to determine if the complex was formed or inhibited. In this assay a phosphate buffer may be used with 1M NaCl to improve the affinity for the two RNA. The stability of the complex is concentration dependent so that μM concentrations are used and the assay is run at 4 degrees C.

The 5' labeled target RNA sequence (5'-CGGU-GUAAAAGC) is bound to a avidin microtiter plate (Roche High Load plates, 96-well avidin microtiter plates) by adding 150 μl of target solution to each well (FIG. 3, step A). The plates are covered and incubated at 37° C. for 1 hour. The plates are then rinsed twice with binding buffer, the second rinse is incubated at 37° C. for 5 minutes. The plates are then rinsed two additional times with binding buffer, covered, and ready for use.

The test compounds were prepared by thawing solutions of the compounds to room temperature. Dilutions of the test compounds (1:10 and 1:500) were prepared by dilution in DMSO and shaking for 1 hour.

The assays were performed by adding 98.5 μl of loading buffer (100 mM Tris HCl, pH 7.5, 150 mM NaCl and 0.1% Tween 20, pH adjusted from around 4.5 to 7.5 with 10 M NaOH) to each well of the plate. Test compounds were added individually to each well (1.5 μl each), and the plates were mixed for 1 hour (FIG. 3, step B).

Fifty microliters of solution containing the tool tRNA (5'-GCUXUUAYZCUG; where the X, Y, and Z are independently selected from modified nucleosides mnm5s2U, mcm5s2U, ms2t6A, s2U, ψ, and t6A) was then added to each well and the plates were incubated at 4° C. for 1 hour with shaking (FIG. 3, step C). The reaction mixture was then removed, while the mixture was still cold, and the remaining compound solution was also removed.

After removing the remaining solution, reading buffer (50 mM Hepes, pH 7.5, 100 mM NaCl, PEG (40 mg/200 ml)) was then added to each well and the results were read using a plate reader.

As shown in FIG. 3, a positive (+) reaction indicates that the test compound inhibits binding of the tool tRNA to the target nucleic acid (e.g. the test compound binds to either the tool tRNA, the target nucleic acid molecule or both the tool tRNA and the target nucleic acid molecule). A negative (−) reaction indicates that the test compound does not inhibit the binding of the tool tRNA to the target nucleic acid (e.g. the test compound does not bind to either the tool tRNA or the target nucleic acid).

In the AlphaScreen configuration (FIG. 3) the assay is done in solution using the same RNA as the immobilization assay. The donor and acceptor beads are bound to their respective RNA's. During the screening the RNAs and test drugs/small molecules are incubated together and formation of the complex is measured using the AlphaScreen detection conditions. Utilization of the AlphaScreen assay may allow for the assay to be run at a lower RNA concentration at room temperature, and increase the stability of the complex.

These screening methods can be used to evaluate the compounds described herein for their anti-HIV activity, including against drug-resistant HIV strains.

Example III. Biological Activity of the Compounds Described Herein

The screening assay described above was carried out on a combinatorial library of compounds, and the following lead compounds were identified.

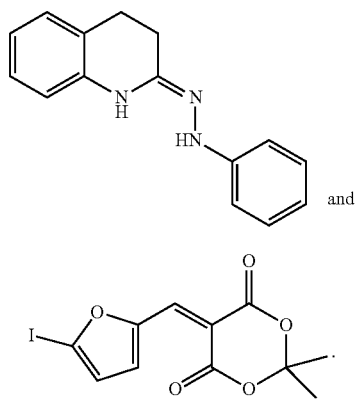

(Compound 154) and (Compound 156)

These compounds were further screened for activity in HIV-1-infected peripheral blood mononuclear cells (PBMC). The data (experiments were repeated, so duplicates are shown) is summarized in the tables below, and also in FIGS. 4A-B and 5A-B.

INHIBITION OF HIV-1 BA-L REPLICATION IN PBMC BY HIT #164

| | CONC (μm) | | | | | | | | | |
|---|---|---|---|---|---|---|---|---|---|---|
| | 0.0 | 0.01 | 0.03 | 0.10 | 0.32 | 1.00 | 3.16 | 10.0 | 31.6 | 100 |
| | RT Values (cpm) | | | | | | | | | |
| SAMPLE 1 | 3795 | 9824 | 207 | 3464 | 2554 | 115 | 221 | 180 | 52 | 64 |
| SAMPLE 2 | 8838 | 211 | 49 | 195 | 103 | 61 | 10 | 16 | 0 | 8 |
| SAMPLE 3 | 3910 | 8639 | 7537 | 8146 | 4990 | 4868 | 2112 | 1678 | 1622 | 252 |
| MEAN | 5514.6 | 6224.9 | 2597.9 | 3935.3 | 2549.3 | 1681.6 | 781.3 | 624.9 | 558.2 | 108.3 |

-continued

| | | | | | | | | | | |
|---|---|---|---|---|---|---|---|---|---|---|
| % VC | 100.0 | 112.9 | 47.1 | 71.4 | 46.2 | 30.5 | 14.2 | 11.3 | 10.1 | 2.0 |
| TOXICITY VALUES (Cell Titer 96 - O.D. @ 490/650 nm) | | | | | | | | | | |
| SAMPLE 1 | 1.959 | 2.305 | 2.185 | 2.152 | 2.259 | 2.040 | 2.102 | 2.109 | 1.681 | 1.788 |
| SAMPLE 2 | 1.815 | 1.784 | 1.824 | 1.716 | 1.757 | 1.699 | 1.758 | 1.813 | 1.747 | 1.515 |
| SAMPLE 3 | 1.745 | 1.815 | 1.754 | 1.844 | 1.836 | 1.930 | 1.955 | 1.934 | 1.999 | 1.806 |
| MEAN | 1.840 | 1.968 | 1.921 | 1.904 | 1.951 | 1.890 | 1.938 | 1.952 | 1.875 | 1.703 |
| % CC | 100.0 | 107.0 | 104.4 | 103.5 | 106.0 | 102.7 | 105.4 | 106.1 | 101.9 | 92.6 |

| DRUG: HIT #154 | 50% | 90% | 95% |
|---|---|---|---|
| TC (μM) | >100 | >100 | >100 |
| IC (μM) | 0.27 | 32.1 | 65.1 |
| ANTIVIRAL INDEX (AI) | ?372 | >3.11 | >1.54 |

Inhibition of HIV-1 Ba-L Replication in PBMC by Hit #154

| | CONC (μM) | | | | | | | | | |
|---|---|---|---|---|---|---|---|---|---|---|
| | 0.0 | 0.01 | 0.03 | 0.10 | 0.32 | 1.00 | 3.16 | 10.0 | 31.6 | 100 |
| RT Values(cpm) | | | | | | | | | | |
| SAMPLE1 | 28463 | 31907 | 28419 | 24503 | 30361 | 18120 | 12447 | 13978 | 10815 | 3062 |
| SAMPLE2 | 26265 | 25645 | 27673 | 28356 | 24204 | 21373 | 16921 | 10363 | 7472 | 2720 |
| SAMPLE3 | 33625 | 29785 | 32092 | 33522 | 29638 | 17704 | 16058 | 12882 | 8974 | 1622 |
| MEAN | 29451.0 | 29112.2 | 29394.5 | 28793.5 | 28067.5 | 19065.5 | 15141.8 | 12407.5 | 9086.8 | 2467.8 |
| % VC | 100.0 | 98.8 | 99.8 | 97.8 | 95.3 | 64.7 | 51.4 | 42.1 | 30.9 | 8.4 |
| TOXICITY VALUES (Cell Titer 96 - O.D. @ 490/650 nm) | | | | | | | | | | |
| SAMPLE1 | 0.780 | 1.163 | 0.746 | 1.086 | 0.736 | 1.296 | 1.146 | 0.712 | 0.898 | 0.757 |
| SAMPLE2 | 0.829 | 1.007 | 0.831 | 0.970 | 1.231 | 1.045 | 0.903 | 1.254 | 1.018 | 0.854 |
| SAMPLE3 | 0.874 | 0.800 | 0.853 | 0.843 | 0.845 | 0.892 | 0.843 | 0.846 | 0.970 | 0.697 |
| MEAN | 0.827 | 0.990 | 0.810 | 0.966 | 0.937 | 1.077 | 0.964 | 0.937 | 0.962 | 0.769 |
| % CC | 100.0 | 119.6 | 97.9 | 116.8 | 113.3 | 130.2 | 116.5 | 113.2 | 116.3 | 92.9 |

| DRUG: HIT #154 | 50% | 90% | 95% |
|---|---|---|---|
| TC (μM) | >100 | >100 | >100 |
| IC (μM) | 3.77 | 92.0 | >100 |
| ANTIVIRAL INDEX (AI) | >26.6 | >1.09 | — |

Inhibition of HIV-1 Ba-L Replication in PBMC by Hit #156

| | CONC (μM) | | | | | | | | | |
|---|---|---|---|---|---|---|---|---|---|---|
| | 0.0 | 0.01 | 0.03 | 0.10 | 0.32 | 1.00 | 3.16 | 10.0 | 31.6 | 100 |
| RT Values(cpm) | | | | | | | | | | |
| SAMPLE1 | 9507 | 10480 | 6505 | 8064 | 8253 | 9732 | 6132 | 635 | 54 | 18 |
| SAMPLE2 | 9758 | 8884 | 8625 | 6238 | 7009 | 5647 | 1058 | 579 | 94 | 2 |
| SAMPLE3 | 8572 | 11894 | 8243 | 4871 | 7376 | 2583 | 586 | 575 | 290 | 0 |
| MEAN | 9279.1 | 10418.9 | 7790.6 | 6390.6 | 7545.6 | 5986.9 | 2591.6 | 595.9 | 145.6 | 6.4 |
| % VC | 100.0 | 112.3 | 84.0 | 68.9 | 81.3 | 64.5 | 27.9 | 6.4 | 1.6 | 0.1 |
| TOXICITY VALUES (Cell Titer 96 - O.D. @ 490/650 nm) | | | | | | | | | | |
| SAMPLE1 | 1.868 | 2.344 | 2.336 | 2.142 | 2.234 | 2.065 | 2.179 | 2.172 | 2.078 | 1.651 |
| SAMPLE2 | 1.760 | 1.718 | 1.807 | 1.855 | 1.808 | 1.819 | 1.770 | 1.791 | 1.741 | 1.594 |
| SAMPLE3 | 1.714 | 1.852 | 1.831 | 1.858 | 1.768 | 1.762 | 1.792 | 1.810 | 1.855 | 1.594 |
| MEAN | 1.781 | 1.971 | 1.991 | 1.952 | 1.937 | 1.882 | 1.914 | 1.924 | 1.891 | 1.613 |
| % CC | 100.0 | 110.7 | 111.8 | 109.6 | 108.8 | 105.7 | 107.5 | 108.1 | 106.2 | 90.6 |

| DRUG: HIT #156 | 50% | 90% | 95% |
|---|---|---|---|
| TC (μM) | >100 | >100 | >100 |
| IC (μM) | 1.58 | 8.26 | 14.0 |
| ANTIVIRAL INDEX (AI) | >63.3 | >12.1 | >7.14 |

Inhibition of HIV-1 Ba-L Replication in PBMC by

Figure 6A:
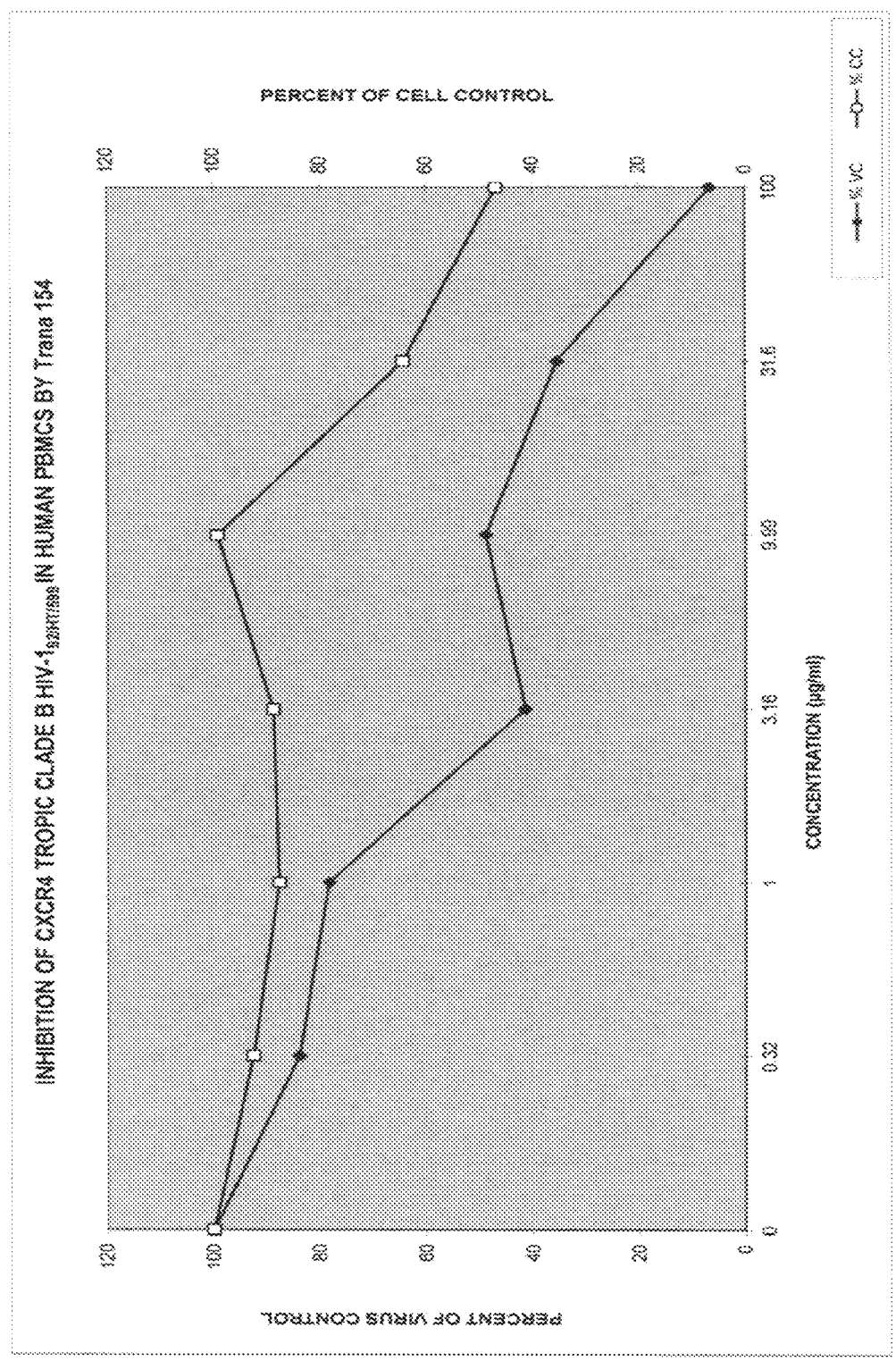
FIGS. 6A-C are charts summarizing data obtained for two compounds using an example of the HIV assay, versus an AZT control (FIG. 6C).
Figure 6B:
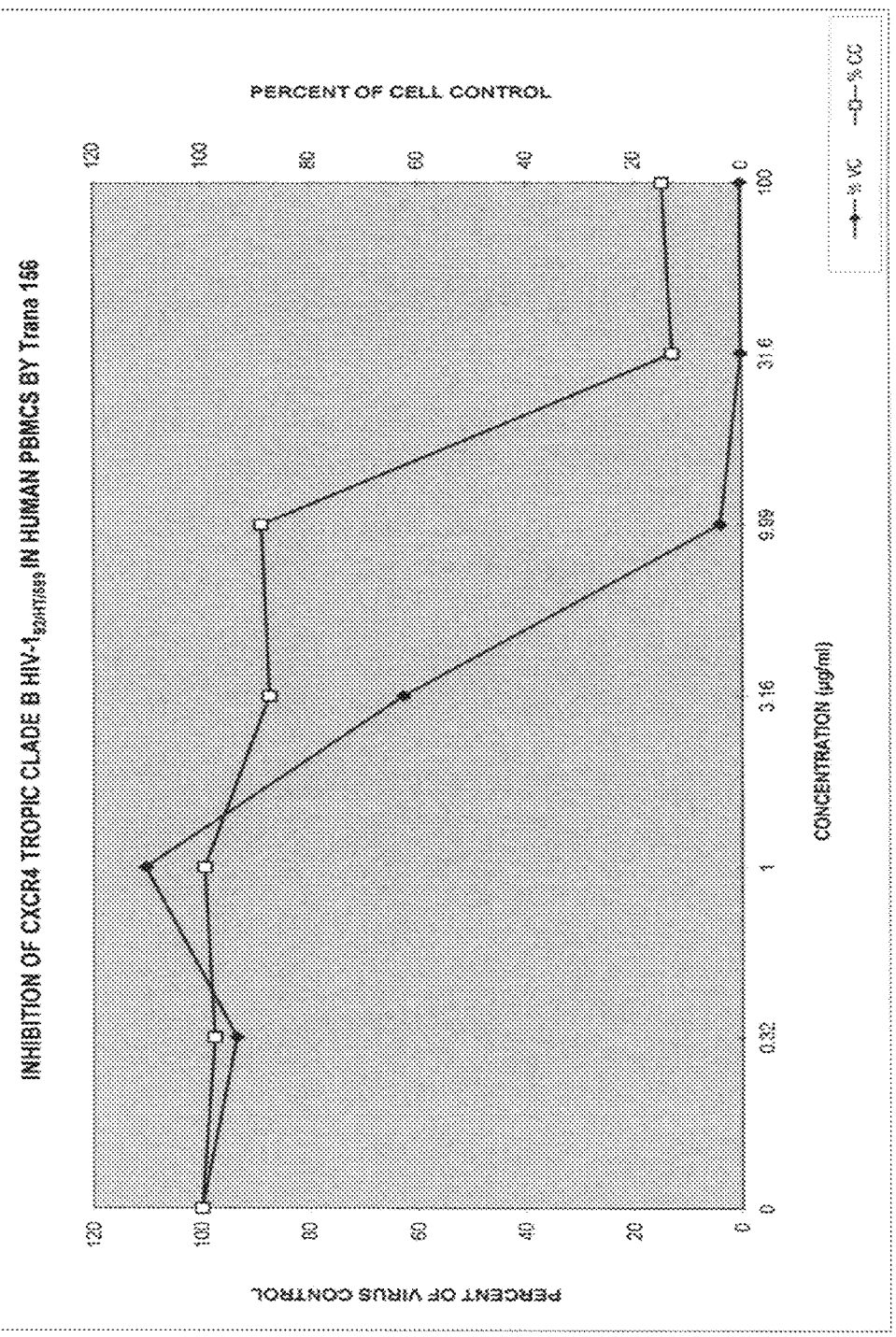
Figure 6C:
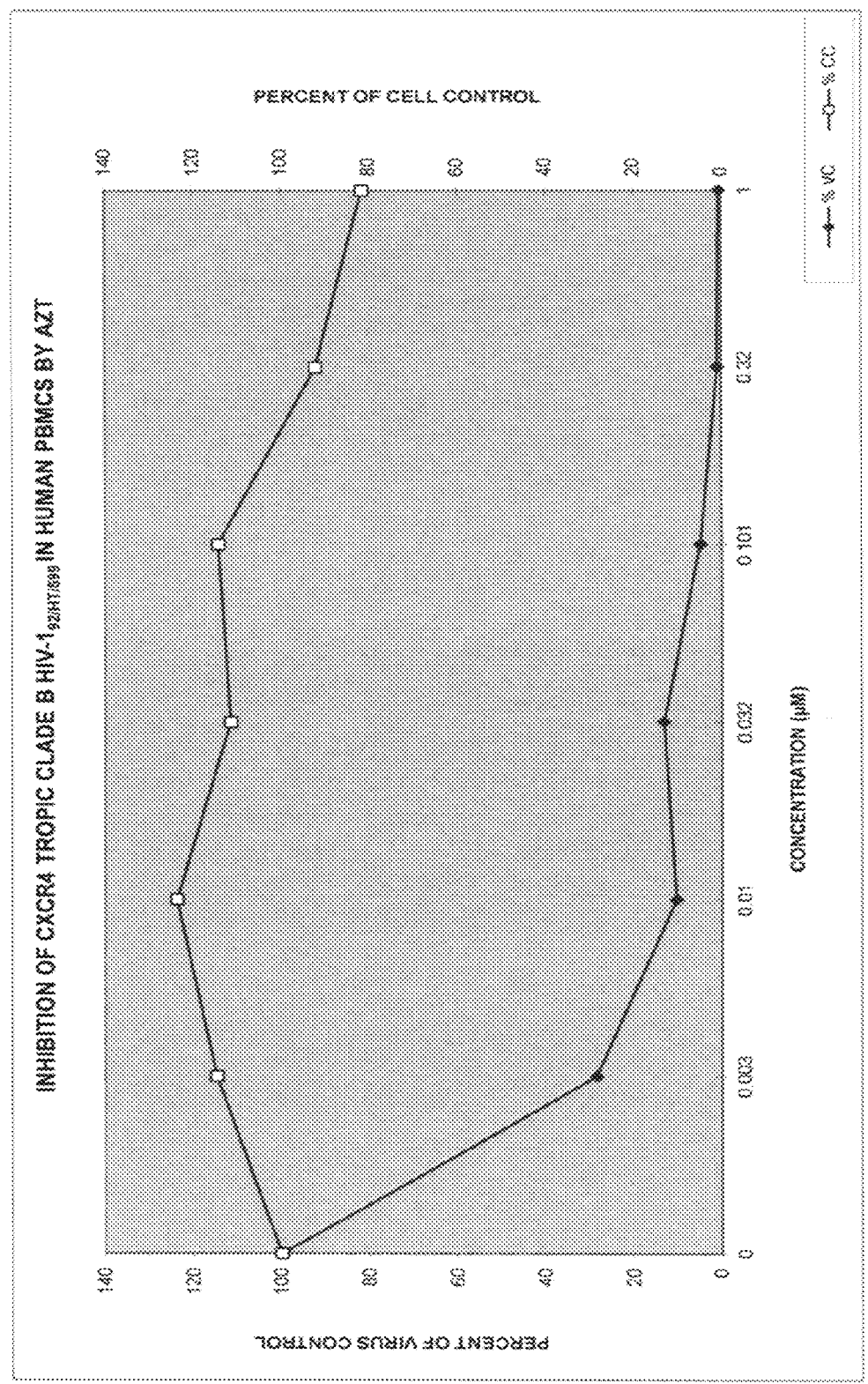

Hit #156 control wells and virus control wells in parallel with the experimental wells. After 7 days in culture, efficacy was evaluated by measuring the reverse transcriptase in the culture supernatants and the cells were stained with the tetrazolium dye XTT to evaluate cytotoxicity. The data is shown below in the following tables, and in FIGS. 6A-C.

|  | CONC (μM) | | | | | | | | | |
|---|---|---|---|---|---|---|---|---|---|---|
|  | 0.0 | 0.01 | 0.03 | 0.10 | 0.32 | 1.00 | 3.16 | 10.0 | 31.6 | 100 |
| RT Values(cpm) | | | | | | | | | | |
| SAMPLE1 | 26918 | 25643 | 25769 | 38847 | 18012 | 21965 | 6829 | 9437 | 120 | 0 |
| SAMPLE2 | 25877 | 28270 | 26494 | 24637 | 26707 | 22751 | 9899 | 247 | 1345 | 0 |
| SAMPLE3 | 28956 | 33067 | 29027 | 36331 | 25800 | 25042 | 18609 | 585 | 378 | 2 |
| MEAN | 27250.2 | 28993.3 | 27096.7 | 33271.7 | 23506.3 | 23252.7 | 11779.0 | 3423.0 | 614.3 | 0.7 |
| % VC | 100.0 | 106.4 | 99.4 | 122.1 | 86.3 | 85.3 | 43.2 | 12.6 | 2.3 | 0.0 |
| TOXICITY VALUES (Cell Titer 96 - O.D. @ 490/650 nm) | | | | | | | | | | |
| SAMPLE1 | 0.759 | 0.687 | 0.821 | 1.098 | 1.094 | 1.173 | 1.161 | 1.001 | 0.997 | 0.795 |
| SAMPLE2 | 0.741 | 1.030 | 1.115 | 1.053 | 1.234 | 1.067 | 1.175 | 0.993 | 1.014 | 0.787 |
| SAMPLE3 | 0.603 | 0.777 | 0.798 | 0.822 | 0.765 | 0.789 | 0.845 | 0.934 | 0.926 | 0.978 |
| MEAN | 0.768 | 0.831 | 0.911 | 0.991 | 1.031 | 1.010 | 1.060 | 0.976 | 0.979 | 0.847 |
| % CC | 100.0 | 108.3 | 118.7 | 129.1 | 134.3 | 131.5 | 138.1 | 127.1 | 127.5 | 110.3 |

| DRUG: HIT #156 | 50% | 90% | 95% |
|---|---|---|---|
| TC (μM) | >100 | >100 | >100 |
| IC (μM) | 2.63 | 13.3 | 23.3 |
| ANTIVIRAL INDEX (AI) | >38.1 | >7.51 | >4.30 |

The HIV strain was HIV-1/Ba-L. The titer was 0.1 μL/well. The inhibition of HIV-1/Ba-L replication in PBMC, versus control, is shown in FIGS. 4A-B and 5A-B.

The two compounds demonstrated anti-HIV activity based on the above-referenced data, which was obtained at Southern Research Institute. Repeat studies were performed at ImQuest BioSciences using PBMC cell lines and duplicated the data noted above.

In these studies, PHA-P stimulated PBMCs from three donors were pooled together and re-suspended in fresh tissue culture medium at $1.\times 10^{6}$ cells/mL and plated in the interior wells of a 96 well round bottom microplate at 50 μl/well. A 100 μL volume of 9 concentrations of compound serially diluted were transferred to the round-bottom 96 well plate containing the cells in triplicate. Fifty microliters (μL) of HIV-1 at a pre-determined dilution was added. Each plate contained cell

| Compounds | HIV-1$_{92HT599}$ | | |
|---|---|---|---|
|  | EC$_{50}$ | TC$_{50}$ | TI |
| Trana 154 (μg/ml) | 2.42 | 81.7 | 33.76 |
| Trana 156 (μg/ml) | 4.06 | 18.0 | 4.43 |
| AZT (μM) | <0.003 | >1.0 | >333.33 |

Raw Data Trana 154

|  | Conc (μg/ml) | | | | | | |
|---|---|---|---|---|---|---|---|
|  | 0 | 0.32 | 1 | 3.16 | 9.99 | 31.6 | 100 |
| RLU (Relative Light Units) | | | | | | | |
| SAMPLE 1 | 9807.5 | 27495.0 | 10410.0 | 11407.0 | 13230.0 | 5800.0 | 1021.0 |
| SAMPLE 2 | 20490.0 | 14218.0 | 21914.0 | 10934.0 | 13148.0 | 7652.0 | 744.0 |
| SAMPLE 3 | 27765.0 | 6891.0 | 13031.0 | 1649.0 | 1933.0 | 7462.0 | 2139.0 |
| TOXICITY VALUES (XTT - O.D. @ 450/650 nm) | | | | | | | |
| SAMPLE 1 | 1.0248 | 1.0510 | 1.0187 | 1.0889 | 0.9242 | 0.6005 | 0.5742 |
| SAMPLE 2 | 1.1461 | 1.0896 | 0.9670 | 0.9881 | 1.2189 | 0.7620 | 0.5461 |
| SAMPLE 3 | 1.1881 | 0.9729 | 0.9683 | 0.9103 | 1.1959 | 0.6103 | 0.4574 |
| Virus: | HIV-1 | | Clade: | B | | | |
| Strain: | 92/HT/599 | | Cells: | HUMAN PBMCS | | | |
| Tropism: | CXCR4 | | Project #: | 277-01 | | | |

Antiviral Compound Trana 154

|  | 25% | 50% | 95% |
|---|---|---|---|
| EC$_{50}$ (µg/ml) | 1.11 | 2.42 | >100 |
| TC$_{50}$ (µg/ml) | 22.3 | 81.7 | >100 |
| Therapeutic Index (TI) | 20.09 | 33.76 | 1 |

| | Antiviral Test Values | | | Cytotoxicity Test Values | | |
|---|---|---|---|---|---|---|
| Conc (µg/ml) | Mean RLU | St. Dev. | % Virus Control | Mean OD @ 450/650 nm | St. Dev. | % Cell Viability |
| 0 | 19287.5 | 9138.2825 | 100.00 | 1.120 | 0.08512551 | 100.00 |
| 0.32 | 16201.3 | 10444.205 | 84.00 | 1.038 | 0.05945371 | 92.64 |
| 1 | 15121.3 | 6025.8507 | 78.40 | 0.983 | 0.02832119 | 87.74 |
| 3.16 | 7996.7 | 5502.3255 | 41.46 | 0.995 | 0.0896395 | 88.82 |
| 9.99 | 9436.3 | 6498.213 | 48.92 | 1.113 | 0.16390952 | 99.35 |
| 31.6 | 6841.0 | 1154.4232 | 35.47 | 0.721 | 0.09903126 | 64.38 |
| 100 | 1301.3 | 738.54339 | 6.75 | 0.526 | 0.06096384 | 46.94 |

| | Conc (µg/ml) | | | | | |
|---|---|---|---|---|---|---|
| | 0 | 0.32 | 1 | 3.16 | 9.99 | 31.6 | 100 |
| RLU (Relative Light Units) | | | | | | |
| SAMPLE 1 | 9607.5 | 9520.0 | 24338.0 | 9530.0 | 138.0 | 46.0 | 68.0 |
| SAMPLE 2 | 20490.0 | 22416.0 | 22848.0 | 14041.0 | 48.0 | 42.0 | 62.0 |
| SAMPLE 3 | 27765.0 | 22210.0 | 16689.0 | 12746.0 | 2214.0 | 36.0 | 52.0 |
| TOXICITY VALUES (XTT - O.D. @ 450/650 nm) | | | | | | |
| SAMPLE 1 | 1.0248 | 1.0465 | 1.1281 | 0.9762 | 1.1309 | 0.1469 | 0.1657 |
| SAMPLE 2 | 1.1461 | 1.0465 | 1.1281 | 0.9762 | 1.1309 | 0.1469 | 0.1657 |
| SAMPLE 3 | 1.1881 | 1.1893 | 1.0879 | 0.9889 | 0.7293 | 0.1399 | 0.1646 |

| Virus: | HIV-1 | Clade: | B |
|---|---|---|---|
| Strain: | 92/HT/599 | Cells: | HUMAN PBMCS |
| Tropism: | CXCR4 | Project #: | 277-01 |

Antiviral Compound: Trana 156

|  | 25% | 50% | 95% |
|---|---|---|---|
| EC (µg/ml) | 2.35 | 4.06 | 9.82 |
| TC (µg/ml) | 12.3 | 18.0 | <100 |
| Therapeutic Index (TI) | 5.23 | 4.43 | <10.18 |

| | Antiviral Test Values | | | Cytotoxicity Test Values | | |
|---|---|---|---|---|---|---|
| Conc (µg/ml) | Mean RLU | St. Dev. | % Virus Control | Mean OD @ 450/650 nm | St. Dev. | % Cell Viability |
| 0 | 19287.5 | 9138.28246 | 100.00 | 1.120 | 0.085126 | 100.00 |
| 0.32 | 18048.7 | 7386.76014 | 93.58 | 1.094 | 0.082446 | 97.66 |
| 1 | 21291.7 | 4055.04998 | 110.39 | 1.115 | 0.023209 | 99.50 |
| 3.16 | 12105.7 | 2322.67095 | 62.76 | 0.980 | 0.007332 | 87.52 |
| 9.99 | 800.0 | 1225.38647 | 4.15 | 0.997 | 0.231864 | 89.00 |
| 31.6 | 41.3 | 5.03322296 | 0.21 | 0.145 | 0.004041 | 12.90 |
| 100 | 60.7 | 8.08290377 | 0.31 | 0.165 | 0.000635 | 14.76 |

Raw Data (AZT)

| | Conc (μg/ml) | | | | | |
|---|---|---|---|---|---|---|
| | 0 | 0.003 | 0.01 | 0.032 | 0.101 | 0.32 | 1 |
| RLU (Relative Light Units) | | | | | | |
| SAMPLE 1 | 9607.5 | 3755.0 | 518.0 | 2047.0 | 132.0 | 52.0 | 98.0 |
| SAMPLE 2 | 20490.0 | 2065.0 | 4220.0 | 862.0 | 1555.8 | 360.0 | 98.0 |
| SAMPLE 3 | 27786.0 | 10890.0 | 1259.0 | 4987.0 | 1123.0 | 120.0 | 142.0 |
| TOXICITY VALUES (XTT - O.D. @ 450/650 nm) | | | | | | |
| SAMPLE 1 | 1.0248 | 1.2949 | 1.2850 | 1.2908 | 1.1598 | 0.9984 | 0.5742 |
| SAMPLE 2 | 1.1481 | 1.3058 | 1.6369 | 1.1569 | 1.3250 | 1.1398 | 1.0479 |
| SAMPLE 3 | 1.1861 | 1.2555 | 1.2369 | 1.2990 | 1.3287 | 0.9607 | 1.1224 |

| | | | | |
|---|---|---|---|---|
| Virus: | HIV-1 | | Clade: | B |
| Strain: | 92/HT/599 | | Cells: | HUMAN PBMCS |
| Tropism: | CXCR4 | | Project #: | 277-01 |

Antiviral Compound: AZT

Antiviral Compound: AZT

| | 25% | 50% | 95% |
|---|---|---|---|
| EC (μM) | <0.00300 | <0.00300 | 0.0990 |
| TC (μM) | >1.0 | >1.0 | >1.0 |
| Therapeutic Index (TI) | >333.33 | >333.33 | >10.10 |

| | Antiviral Test Values | | | Cytotoxicity Test Values | | |
|---|---|---|---|---|---|---|
| Conc (μM) | Mean RLU | St. Dev. | % Virus Control | Mean OD @ 450/650 nm | St. Dev. | % Cell Viability |
| 0 | 19287.5 | 9138.28246 | 100.00 | 1.120 | 0.085126 | 100.00 |
| 0.003 | 5503.7 | 4570.19916 | 28.53 | 1.285 | 0.026461 | 114.74 |
| 0.01 | 1999.0 | 1958.80091 | 10.36 | 1.386 | 0.218383 | 123.74 |
| 0.032 | 2538.7 | 2243.28071 | 13.16 | 1.249 | 0.079727 | 111.47 |
| 0.101 | 936.7 | 729.569965 | 4.86 | 1.281 | 0.07909 | 114.36 |
| 0.32 | 190.7 | 147.313724 | 0.99 | 1.033 | 0.094421 | 92.20 |
| 1 | 112.7 | 25.4034118 | 0.56 | 0.915 | 0.29734 | 81.66 |

In one embodiment, the compounds as described herein include all analogs shown in Formulas I and II other than the two compounds identified above. In another embodiment, the compounds described herein include the two compounds identified above.

Although the foregoing invention has been described in some detail by way of illustration and example for purposes of clarity of understanding, it will be obvious that certain changes and modifications may be practiced within the scope of the appended claims.

What is claimed is:

1. A method of treating or preventing a retroviral an HIV infection, comprising administering an inhibitor of retroviral propagation a compound of Formula II:

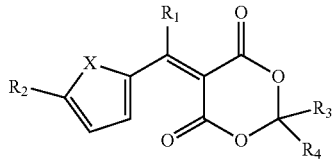

Formula II wherein:
$R^1$ is hydrogen or $C_{1-6}$ alkyl,
$R^2$ is selected from the group consisting of hydrogen, $C_{1-6}$ alkyl, $C_{1-6}$ haloalkyl, and halo,
$R^3$ and $R^4$, are, independently, the same or different, and are selected from the group consisting of hydrogen and $C_{1-6}$ alkyl,
and
X is O or S,
and pharmaceutically acceptable salts thereof.

2. The method of claim 1, wherein the inhibitor inhibits retroviral reverse transcription.

3. The method of claim 1, wherein the inhibitor inhibits viral recruitment of the retroviral primer used in translation, human tRNA$^{Lys3}$.

4. The method of claim 1, wherein the inhibitor inhibits the final packaging and assembly of new virions.

5. The method of claim 1, wherein the inhibitor inhibits the binding of a host cell tRNA to a target nucleic acid molecule.

6. The method of claim 1, further comprising the co-administration of a second anti-HIV compound.

7. The method of claim 6, wherein the second anti-HIV compound is selected from the group consisting of NRTIs, NNRTIs, VAP anti-idiotypic antibodies, CD4 and CCR5 receptor inhibitors, entry inhibitors, antisense oligonucleotides, ribozymes, protease inhibitors, neuraminidase inhibitors, tyrosine kinase inhibitors, PI-3 kinase inhibitors, and Interferons.

8. The method of claim 1, wherein the HIV is selected from the group consisting of HIV-I, HIV-II, HIV-III (also known as HTLV-II, LAV-I, LAV-2), and mutated versions thereof.

9. The method of claim 6, wherein the additional antiviral agent is an entry inhibitor, reverse transcriptase inhibitor, protease inhibitor, or an immune-based therapeutic agent.

* * * * *